United States Patent
Stuerzinger et al.

(10) Patent No.: US 8,954,154 B2
(45) Date of Patent: Feb. 10, 2015

(54) WIRELESS CARDIORESONANCE STIMULATION

(71) Applicant: Cardiola Ltd., Winterthur (CH)

(72) Inventors: Christian Stuerzinger, Winterthur (CH); Larry Lapanashvili, Winterthur (CH); Thomas Zimmermann, Schaffhausen (CH); Armin Eggli, Uhwiesen (CH); Christian Piguet, Neuchatel (CH); Jean-Felix Perotto, Neuchatel (CH)

(73) Assignee: Cardiola Ltd., Winterthur (CH)

( * ) Notice: Subject to any disclaimer, the term of this patent is extended or adjusted under 35 U.S.C. 154(b) by 0 days.

(21) Appl. No.: 14/331,127

(22) Filed: Jul. 14, 2014

(65) Prior Publication Data

US 2014/0350638 A1   Nov. 27, 2014

Related U.S. Application Data

(60) Continuation of application No. 14/032,168, filed on Sep. 19, 2013, now Pat. No. 8,812,118, which is a division of application No. 11/667,622, filed as application No. PCT/EP2005/009384 on Aug. 31, 2005, now Pat. No. 8,577,471.

(30) Foreign Application Priority Data

Nov. 16, 2004  (EP) .................................... 04027227

(51) Int. Cl.
*A61N 1/00* (2006.01)
*A61N 1/36* (2006.01)
*A61N 1/372* (2006.01)

(52) U.S. Cl.
CPC ........ *A61N 1/36003* (2013.01); *A61N 1/37217* (2013.01)

USPC .......................................................... 607/48

(58) Field of Classification Search
USPC .......................................................... 607/48
See application file for complete search history.

(56) References Cited

U.S. PATENT DOCUMENTS 4,541,417 A   9/1985   Krikorian
5,540,235 A   7/1996   Wilson
(Continued)

FOREIGN PATENT DOCUMENTS

DE   199 29 380 A1   12/2000
WO   01/13990 A1   3/2001

*Primary Examiner* — Robert N Wieland
(74) *Attorney, Agent, or Firm* — Kilpatrick Townsend & Stockton LLP

(57) ABSTRACT

An apparatus for the cardio-synchronized stimulation of skeletal or smooth muscle, but excluding the heart muscles, in a counterpulsation mode of a patient. The apparatus comprises an active and a passive electrode for attachment to said patient, a signal processor having a configuration input for varying a time delay associated with counterpulsation mode stimulation, and a sensing system for sensing information relating to the performance of the patient's heart and for transmission of information signals to said signal processor, said signal processor producing control signal information relating to stimulation signals to be applied to said active electrode in a counterpulsation mode, a stimulation signal generator Associated with said active electrode for generating stimulation signals, wireless transmission means for transmitting said control signal information from said signal processor to said stimulation signal generator whereby said stimulation signal generator applies stimulation signals to said active electrode in accordance with said signal information.

19 Claims, 17 Drawing Sheets

(56) References Cited

U.S. PATENT DOCUMENTS

| | | |
|---|---|---|
| 6,442,432 B2 | 8/2002 | Lee |
| 6,450,942 B1 | 9/2002 | Lapanashvili et al. |
| 6,662,052 B1 | 12/2003 | Sarwal et al. |
| 7,120,484 B2 | 10/2006 | Lu et al. |
| 7,403,821 B2 | 7/2008 | Haugland et al. |
| 2003/0135125 A1* | 7/2003 | Lu et al. .................. 600/510 |
| 2003/0144710 A1 | 7/2003 | Haugland et al. |
| 2005/0136385 A1 | 6/2005 | Mann et al. |

* cited by examiner

QT = Delay
A = Amplitude
W = Impulse Width
I = Interval

WIRELESS CARDIORESONANCE STIMULATION

CROSS-REFERENCES TO RELATED APPLICATION

This application is a continuation of U.S. patent application Ser. No. 14/032,168, filed Sep. 19, 2013, now U.S. Pat. No. 8,812,118, which is a divisional of U.S. patent application Ser. No. 11/667,622, filed Dec. 14, 2007, now U.S. Pat. No. 8,577,471, which claims the priority of International Patent Application PCT/EP2005/009384, filed Aug. 31, 2005, which claims the benefit of European Patent Application 04027227.0, filed Nov. 16, 2004, the disclosures of which are hereby incorporated in their entirety by reference for all purposes.

BACKGROUND OF THE INVENTION

The present invention relates to an apparatus for the cardio-synchronized stimulation of skeletal or smooth muscle, but excluding the heart muscles, in a counterpulsation mode of a patient having a heart and a cardiovascular system. The patient can be a human being or another mammal such as a race horse, or could also be another animal having a heart and a cardiovascular system such as a kangaroo (kangaroo hearts in good condition can be used for valve replacement in humans).

References in the following to a patient will cover all the foregoing and does not imply the patient is suffering from ill health, since treatments using the present invention can be applied to persons or animals which are not ill but for which a desire exists for improvement in some aspect of their physical or mental condition.

Apparatus and methods of this kind are, for example, described in the International patent application with the publication number WO 01/013990.

The applicants have established that the apparatus and methods described in the above mentioned document WO 01/013990 can be used to advantage for a large number of different applications. A prime application of the apparatus and methods described is improving the condition of the heart of a patient, for example to reduce the likelihood of a heart attack, or to improve the condition of the heart following a heart attack, or to assist the patient in recovering following bypass surgery, or to treat patients with chronic diseases, in particular chronic heart failure and patients suffering from demetabolic syndrome. In addition it has been found that the treatment can be used with minor modifications in order to improve blood flow to various parts of the body and to improve lymph drainage from various parts of the body. Moreover, it has been shown that the treatment can be used to improve the general condition of a wide variety of patients, such as those who are ill or recovering from illness. A wide range of other applications are also known and described in WO 01/013990.

BRIEF SUMMARY OF THE INVENTION

The object of the present invention is to improve the apparatus and methods described in the document WO 01/013990, and in particular to provide a very flexible system which enables a patient to be treated as an outpatient, and indeed also over a long period of time while the patient goes about his normal daily life. It is a further object of the present invention to provide apparatuses and methods which enable the treatment to which any particular patient is subjected to be varied flexibly and for this treatment to take account of developments in this type of treatment which occur during the course of time and which are expected as practical experience in the use of the apparatus and methods grows and the database of successful treatments becomes larger.

A yet further object of the present invention is to minimize the physical size of the apparatus which is associated with the patient, so that it is of light weight, is compact, is easily carried, is reliable and does not hinder the patient in any significant way and so that, for example, the batteries involved have a long working life.

A yet further object of the present invention is to provide an apparatus and methods which enable the patient's reaction to the treatment he is receiving to be monitored remotely and preferably for the treatment to be modified or interrupted if monitoring shows that the treatment is not ideally suited to the particular patient's needs.

In order to satisfy the above object there is provided, in accordance with the present invention, an apparatus of the initially named kind comprising:

- at least one active electrode and at least one passive electrode adapted for attachment to said patient,
- a signal processor preferably having an associated configuration input for varying at least a time delay associated with counterpulsation mode stimulation
- a sensing system for sensing information relating to the performance of the patient's heart and for transmission of information signals to said signal processor,
- said signal processor being adapted to produce control signal information relating to stimulation signals to be applied to said at least one active electrode in a counterpulsation mode,
- a stimulation signal generator associated with said active electrode for generating stimulation signals
- wireless transmission means for transmitting said control signal information from said signal processor to said stimulation signal generator whereby said stimulation signal generator applies stimulation signals to said active electrode in a counterpulsation mode in accordance with said signal information.

The information relating to the performance of the heart is typically selected from the group comprising: heart rate information, ECG information, ECG derived information, ECG information and information resulting from electrical stimulation, ECG derived trigger signals, R-R information, end of T-wave information, blood pressure information and blood pressure derived information.

The sensing system can include at least one of an invasive sensor, an intercavity sensor, a non-invasive sensor, a body surface sensor and a remote sensing system detached from the patient's body.

If a remote sensing system is provided, the signal processor can be integrated into said remote sensing system. The sensing system is however preferably adapted for wireless transmission of said heart information to said signal processor.

Alternatively, the sensing system can be adapted to transmit said heart information to a medical evaluation unit associated with the signal processor and the medical evaluation unit is then preferably adapted to transmit signal configuration information to the signal processor so that said signal processor takes account of said configuration information when generating said control signal information.

Apparatus of the above kind has the advantage that wireless transmission from the signal processor to the stimulation signal generator enables the signal processor to be located remote from the patient and for the stimulation signal generator to be made compact and small because the processing capacity necessary to generate the trigger signals for the stimulation signal generator is located in the separate signal processor and does not have to be carried by the patient. In addition, the batteries associated with the stimulation signal generator carried by the patient do not have to provide the power for the operation of the signal processor and can therefore be made smaller and lighter.

It is particularly beneficial if the sensing system for sensing information relating to the performance of a patient's heart and for transmission of information signals is adapted for wireless transmission of said information signals, either to the signal processor directly or possibly via the medical evaluation unit. If such wireless transmission is used from the sensing system then the patient is completely free of cables connecting him (or her) to the associated apparatus, such as the medical evaluation unit and the signal processor.

For the purpose of the present invention it is sufficient if the sensing system for providing information relating to the performance of the heart simply detects the R-peaks of the patient's heart rhythm and establishes the time at which these peaks occur in order to predict from them the end of the T-wave of the heart rhythm for each successive heartbeat, so that stimulation can be carried out at or close to the predicted end of the T-wave, i.e. in the counterpulsation mode. Such information can be delivered by an electrocardiograph or electrocardioscope but is basically also available from a simple set of ECG electrodes which can be combined with a simple light-weight monitor. Equally, devices are known, such as the "Polar"™ belt or wrist-mounted blood pressure detectors which also reliably provide signal traces related to the patient's heart rhythm and from which information on the R-R peaks and/or the end of the T-wave can be derived. There are also certain remote sensing systems which can deliver corresponding information.

If electrical detection is used, for example using ECG electrodes, then this has the benefit that the electrical stimulation applied to the patient can also be picked up by the ECG electrodes and can be displayed superimposed on the trace of the patient's heart rhythm. In this way the synchronization of the electrical stimulation with the patient's heart rhythm and its effect on the patient's heart rhythm can be better assessed.

It is possible for the sensing system to have its own transmitter for transmitting information relating to the performance of the patient's heart to the signal processor, or to a medical evaluation unit associated with the signal processor, and for the stimulation signal generator to have an antenna for receiving trigger signals and optionally other information from the signal processor.

It is also possible for the transmitter of the sensing system and the receiver of the stimulation signal generator to be combined into a transceiver which is carried by the patient and which is, for example, connected by wires to the sensing system and to the stimulation signal generator. Such transceivers are readily available, for example in the form of a mobile phone. Mobile phones also have the advantage that they have significant signal processing power, so that relevant software can be stored in them as can data relating to the patient's heart rhythm and the performance of the heart and data relating to the stimulation applied or to be applied. Automatic programs can then allow the transmission of such information to a medical evaluation unit at intervals for assessment by a medical practitioner monitoring a number of different patients at the medical evaluation unit. Moreover, it is not essential for a skilled medical practitioner to carry out all evaluations. It is also conceivable for programs to be drawn up which enable at least routine checking to be carried out with a medical practitioner only being alerted if something appears to be amiss.

The signal processor can itself also be realized as a mobile phone or as a dedicated unit similar thereto. This facilitates communication from, for example, a mobile phone associated with the signal sensing system and/or the stimulation signal generator since these two systems, i.e. a mobile phone associated with the sensing system and/or the stimulation signal generator and a mobile phone associated with a signal processor, are inherently compatible. Again, the processing power available in any modern mobile phone system is sufficient for storage of the software programs needed by the signal processor in order to analyze the information coming from the sensing system, to predict the times at which the ends of the T-waves occur and to generate the requisite trigger signals for onward transmission to the stimulation signal generator. If the signal processor is realized as a mobile phone it can be carried by the patient—without the patient being wired to the phone—and the mobile phone forming the signal processor can receive via its inbuilt antenna signals transmitted from an antenna of the sensing system (or from the stimulation signal generator) and can transmit control signals to the stimulation signal generator.

A further advantage of using a mobile phone or a mobile phone-like system is that communication with any other mobile phone or mobile-phone-like system involves a telephone number which can be used to uniquely identify the party with which communication is to be established and the party from whom a communication is received. Thus, one signal processor can communicate with a plurality of different stimulation signal generators, and indeed with a large number of them, and can provide different trigger information and other information to each of them based on the particular needs of the user or on the particular needs of the associated stimulation signal generator.

It is not necessary for this communication to take place simultaneously with a plurality of users but instead the relevant information can be sent batch-wise at discrete times to the individual users. For example, once a timing scheme of trigger signals has been established it can be retained for a period of time so long as the patient's heart rhythm remains substantially constant. Thus, trigger timing information sent by the signal processor to the stimulation signal generator can be stored in a memory of the stimulation signal generator and used cyclically to trigger the electrical stimulation. Since the stimulation signal generator can readily communicate with the sensing system it is also possible for the timing established by the signal processor to be retained and repeatedly used by the stimulation signal generator to apply stimulation to the patient until the sensing system providing heart information shows that something has changed and needs to be reflected by a change in the timing of the trigger signals. Once this happens, the signal processor can be automatically called up to provide changed timing.

It is particularly beneficial that the medical evaluation unit gives medical practitioners the possibility of changing the program used by the signal processor to generate the timing signals. In this way the timing signals supplied by the signal processor to the stimulation signal generator can be adapted in accordance with the patient's needs as assessed by the medical practitioner.

It is particularly favorable if the medical evaluation unit is also realized by incorporating elements of a mobile phone so that communication can take place directly between the medical evaluation unit and the stimulation signal generator. For example, should the medical practitioner sense personally, or in response to an alarm signal generated at the medical evaluation unit, that a treatment being used on a particular patient is not satisfactory or is potentially dangerous, e.g. because of some event, such as an accident, then the ability exists to switch off the stimulation signal generator directly, thus preventing further treatment until such time as the problem has been remedied.

The medical evaluation unit can also be adapted for wireless transmission of the configuration information to said signal processor.

In an alternative embodiment the heart information produced by the sensing system can be sent not to the medical evaluation unit but rather by wireless transmission to the signal processor and the signal processor can be adapted to transmit said heart information to the medical evaluation unit (by wire or by wireless transmission). Likewise the medical evaluation unit can then be adapted to transmit signal configuration information to the signal processor by wire or by wireless transmission and the signal processor then takes account of said configuration information when generating said signal information.

In a particularly preferred embodiment a plurality of active electrodes is provided, each having a respective stimulation signal generator, and the signal processor is adapted to transmit a respective control signal uniquely associated with one of said active electrodes to each said stimulation signal generator. For example, the active electrodes can each have a respective stimulation signal generator connected thereto via a respective lead.

Alternatively, a respective lead can be provided for each active electrode and means can be associated with a single stimulation signal generator for applying stimulation signals to said active electrodes in sequence via said leads.

When the signal processor has a single transmitter adapted to transmit control signal information to a plurality of stimulation signal generators, means are provided for uniquely associating particular control signals with a respective one of said stimulation signal generators.

Alternatively, the signal processor can have a plurality of transmitters each adapted to transmit control signal information to a respective one or group of said stimulation signal generators. In the latter case means are provided for uniquely associating particular control signals with a respective one of said stimulation signal generators.

The signal processor is preferably adapted to transmit control signal information for a train of stimulation signals applied to an active electrode, said control signal information being selected from the group comprising:
amplitude of the stimulation signals,
frequency of the stimulation signals,
duration of the train of the stimulation signals, width of the individual stimulation signals of the train
delay of the train of the stimulation signals relative to a reference selected for counterpulsation stimulation and
a recognition code by which said stimulation signal generator recognizes that said control signal information is intended for it.

As indicated above, means is preferably provided at said stimulation signal generator or at each said stimulation signal generator for storing control signal information relating to any respectively associated active electrode.

It is particularly beneficial when means is provided at said signal processor for transmitting to said stimulation signal generator at least one of a program for processing said control signal information, any subsequent changes to said program and a new program for processing said control signal information.

The or each said stimulation signal generator preferably includes at least some of the following items:
its own controller,
its own clock,
its own receiver antenna (RX),
a power circuit and
a battery.

It is especially beneficial when the or each said stimulation signal generator includes at least one of the following additional items:
a transmitter (TX),
means for data storage,
means for program storage and a
signal generator trigger.

An especially beneficial realization of the invention involves providing the or each said stimulation signal generator with a program and/or hardware providing a wake mode, a sleep mode and a death mode. With such an arrangement the battery associated with the stimulation signal generator only delivers significant amounts of power during the wake mode, but not during the sleep mode from which it can be awakened or during the death mode from which it can no longer be awoken other than by changing or recharging the battery. Such a stimulation signal generator can be switched on and off during even one heartbeat in order to save power and this increases the working life of the battery prior to changing it or recharging it.

It is particularly expedient when a display is provided at least one of said signal processor, said stimulation signal generator and a medical evaluation unit associated with said apparatus, said display being for the display of said heart information signals.

The display can also be adapted to display data representing an image of the electrical stimulation applied to said patient. The display is preferably adapted to display one of an actual ECG-trace and a representation of an ECG-trace with said image of the applied electrical stimulation superimposed thereon.

When a medical evaluation unit is provided it preferably also has an associated printer for printing said display data.

The said sensing system is preferably also adapted to send timing signals to said stimulation signal generator or generators. This enables the synchronization of the trigger signals (especially the stored trigger signals referred to above) with the patient's heart rhythm to be checked.

The sensing system includes a non-electrical sensor and transmits data from said non-electrical sensor to said signal processor. Such a system avoids the electrical stimulation applied to the patient being incorrectly interpreted as heart information.

The sensing system includes an associated signal processor and a transmitter. This enables the signal processor (which can again be part of the mobile phone or of a mobile phone related unit) to compress the heart information and information on electrical stimulation applied to the patient prior to transmission to the signal processor or the medical evaluation unit.

The sensing system can conveniently include at least one of an A/D converter, a data storage memory and a data compressor. At least one of said A/D converter, said data storage memory and said data compressor can be embodied in said associated signal processor.

When the sensing system includes a data compressor for compressing information for transmission to said signal processor or said medical evaluation unit into packages, the signal processor and/or the medical evaluation unit is adapted to assemble said data packages into a continuous data stream, optionally in the form of an ECG-trace with superimposed electrical stimulation signals.

A respective code is preferably uniquely associated with each of said sensing system, said signal processor and said electrical stimulation signal generator or generators, so that each item can be uniquely identified.

The electrical stimulation signal generator preferably has an associated power supply in the form of a battery and a boost converter.

A method of operating an apparatus for the cardio-synchronized stimulation of skeletal or smooth muscles, but excluding the heart muscles, in a counterpulsation mode on a patient having a heart and a cardiovascular system, comprising the steps of using a sensing system providing heart information from the patient to communicate said heart information by wireless means to at least one of a signal processor and a medical evaluation unit adapted to input configuration data to the signal processor and the step of using the signal processor to send trigger data to one or more stimulation signal generators adapted to apply electrical stimulation signals to electrodes provided on or in the patient.

The signal processor can send the trigger data, i.e. the control signal information, to said one or more stimulation signal generators by wireless transmission.

Preferred variants of the apparatus and of the methods are set out in the claims and in the further description.

The invention will now be described in more detail by way of example only and with reference to the accompanying drawings in which are shown:

DETAILED DESCRIPTION OF THE INVENTION

Figure 1:
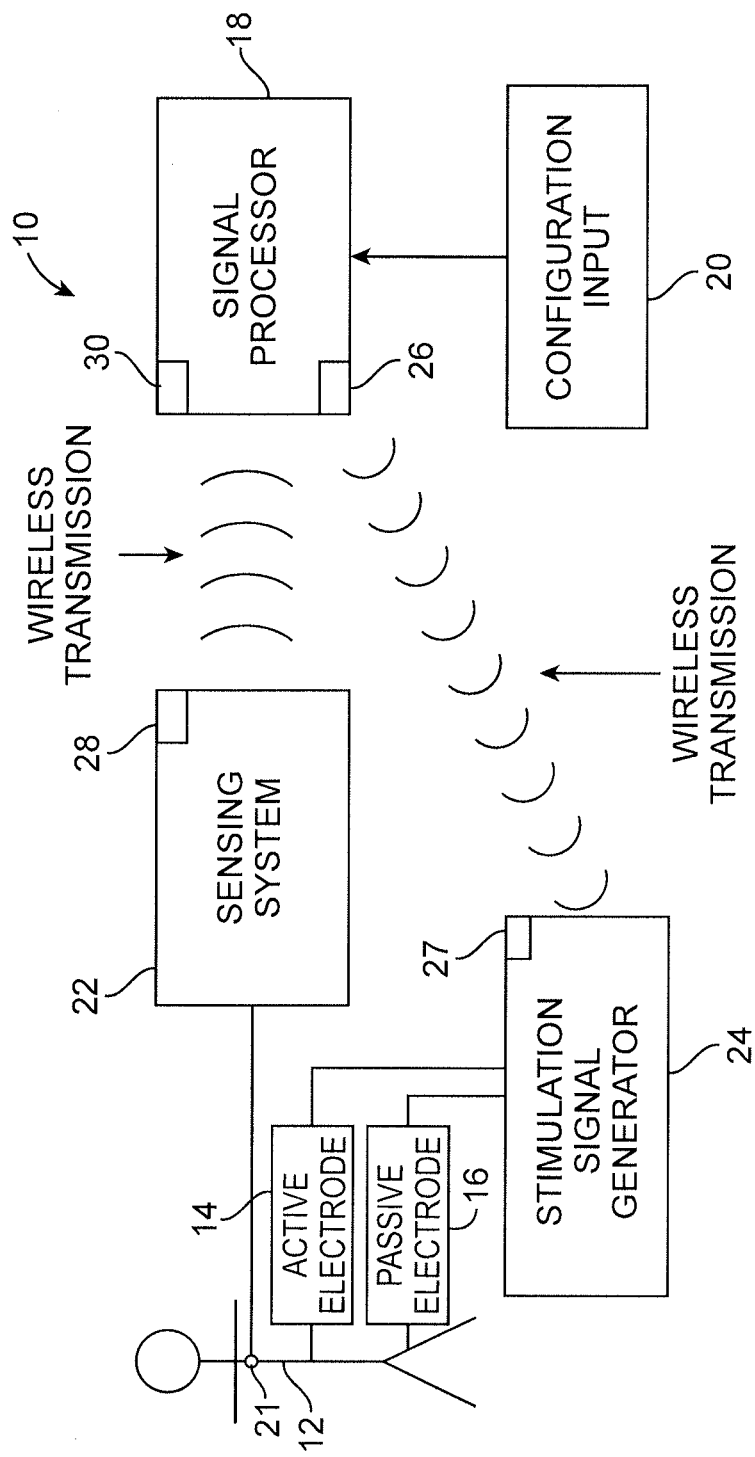
FIG. 1 is a first schematic diagram illustrating the operation of the present invention in accordance with a first embodiment.

In the embodiments of the different figures, the same reference numerals will be used to identify components which are identical to each other or have the same function. It will be understood that the description given for any component having a particular reference numeral in any one of the figures also applies to any component having the same reference numeral in any other figure, unless something is stated to the contrary.

Turning first of all to FIG. 1 there can be seen an apparatus 10 for the cardio-synchronized stimulation of skeletal or smooth muscle present on or in a person 12, or on or in another patient such as a racehorse or on or in an animal, the said person, patient or animal having a heart and a cardiovascular system. The skeletal or smooth muscle can in principle be located anywhere on the body of the patient.

The stimulation is effected typically via electrodes such as 14, 16, e.g. in the manner described in the international patent application with the publication number WO01/013990, or in the manner described in the international patent applications published as WO 2005/044373, WO2005/044374 and WO 2005/044372, or in the EP application EPO4026453.3, all filed on Nov. 8, 2004, the contents of which are incorporated herein by reference.

The apparatus 10 comprises the following items:

at least one active electrode 14 and at least one passive electrode 16 adapted for attachment to the patient 12 being treated, a signal processor 18 having an associated configuration input 20 for varying at least the time delay associated with the counterpulsation mode stimulation, a sensing system 22 for sensing information relating to the performance of the patient's heart and for transmission of information signals to the signal processor 18, the signal processor 18 being adapted to produce control signal information relating to stimulation signals to be applied to said the least one active electrode 14 in the counterpulsation mode, a stimulation signal generator 24 associated with the at least one active electrode for generating the stimulation signals which are applied to the at least one active electrode and wireless transmission means 26 embodied in or associated with the signal processor 18 for transmitting the control signal information from the signal processor 18 to a receiver 27 at the stimulation signal generator 24.

In this way the stimulation signal generator 24 applies stimulation signals to the at least one active electrode in the counterpulsation mode in accordance with the control signal information received from the signal processor 18.

The information relating to the performance of the heart can be of different types and can, e.g., be selected from the group comprising: heart rate information (for example from a "Polar" Belt™), ECG information (e.g. from an electrocardiograph or electrocardioscope), ECG derived information, ECG information and information resulting from electrical stimulation, ECG derived trigger signals, R-R information, end of T-wave information, blood pressure information (e.g. from a blood pressure monitor) and blood pressure derived information.

The said sensing system 22 can include at least one of an invasive sensor, an intercavity sensor, a non-invasive sensor, a body surface sensor and a remote sensing system detached from the patient's body.

The operation of the individual items listed above will now be explained in more detail. As noted above the stimulation is applied in the counterpulsation mode as described in the above referenced WO01/013990. Basically speaking this means that the initial electrical stimulation is applied to the patient at a time corresponding to the end of the T-wave of the patients heart rhythm and more specifically in a time window lying within a range of 5% of the R-R path before the end of the T-wave and 45% of the R-R path after the end of the T-wave.

The precise time at which the initial stimulation is applied via the electrodes to the patient in synchronization with the patient's heart rhythm relative to the end of the T-wave is referred to as the delay. This delay is said to be negative if the stimulation is applied at a time lying within the range of 5% of the R-R path before the end of the T-wave and is positive if the delay is applied within the range of 45% of the R-R path after the end of the T-wave. It is zero if the initial stimulation corresponds with the end of the T-wave. Instead of measuring the delay with respect to the end of the T-wave it is more convenient to measure it from the preceding R-peak, in which case it is always positive.

It will be appreciated by those skilled in the art that the concept of R-R path lengths, corresponding to the distance between successive R-peaks of the heart rhythm, e.g., as displayed on an electrocardiogram, and the point in the electrocardiogram referred to as the end of the T-wave are well established terms in the medical field. They are shown, for example, in FIG. 11A and in FIG. 16B. Furthermore, it will be understood that the actual length of the R-R path, e.g. expressed in milliseconds, is inversely proportional to the patient's heart rate prevailing at any one time and is subject to considerable variation depending on the condition of the heart and on whether the patient is at rest or is exercising, or is excited, is nervous or performing strenuous tasks. The end of the T-wave can be predicted from the times at which the R-peaks occur using the so-called Bazett relationship or by reference to tables of statistics for various categories of persons or patients. When using cardiostimulation in accordance with the present teaching it is necessary to predict, from historical values of the R-R path length, e.g. from the immediately preceding R-R path length, or from a recent average value of the R-R path lengths of several preceding heart beats, when the end of the next T-wave will occur and to time the triggering of the electrical stimulation signals to occur at or near to the predicted end of the T-wave using the appropriate delay.

Ways of predicting the end of the T-wave from past R-R values and a discussion of the difficulties which arise can be found in the aforementioned publication WO 2005/044373. In addition the application published as WO 2005/044374 describes the way a muscle contraction can be prolonged with benefit by applying additional electrical muscle stimulating pulses during each heart beat after the initial stimulating pulse. The application published as WO 2005/044372 describes an apparatus and method by which the electrical stimulating pulses are varied in accordance with a predetermined pattern or randomly in order to avoid a muscle or muscle group to which stimulation is applied for a long time from becoming fatigued. All these techniques require a signal processor such as 18 to determine the timing of the individual electrical stimulating pulses relative to the patient's actual sensed heart rate or rhythm.

As will be explained later it would be unusual to provide just a single active electrode. The prior proposals of the present applicants usually involve four active electrodes associated with a group of muscles and a stimulation signal is applied to each active electrode in turn so that each active electrode receives a stimulation signal every four heart beats. This helps avoid the muscles becoming fatigued or too accustomed to the applied stimulation. Although some of the attached figures show only one active electrode 16, generally a plurality of active electrodes is present as will be explained later. However, the present teaching could be used with just one active electrode. The concept of using multiple active electrodes will be described later with reference to FIGS. 15, 16 and 17

It is convenient for the signal processor 18 to deliver trigger signals which trigger the generation of the actual electrical stimulation signals applied to the patient in the stimulation signal generator. One design for a stimulation signal generator is given in the EP application EPO4026453.3, the content of which is also incorporated herein by reference. Another stimulation signal generator will be described later.

By providing the signal processor 18 separately from the stimulation signal generator 24 it is possible to standardize the stimulation signal generator 24 and to reduce its size so that it can be carried by the patient without being a burden to the patient and without inhibiting his activities in any way. Achieving a further reduction in size of the stimulation signal generator with a simultaneous improvement in its performance is another aim of the present teaching. Yet another aim of the present invention is to enable one stimulation signal generator to be connected to each pair of active and passive electrodes 14 and 16 so that with a plurality of active electrodes 14 a like plurality of stimulation signal generators 24 is present.

Moreover, by adding intelligence to the signal processor 18 it can be made very flexible and adapted to deal with a variety of different circumstances. It can also be reprogrammed to take account of the latest findings, e.g. so as to implement particularly beneficial pulse timings or pulse profiles or particularly beneficial courses of treatment, without having to change the apparatus carried by the patient.

Equally one signal processor 18 can be used with a variety of different sensing systems 22 and can be adapted or updated to derive the information needed from the respective sensing system 22, by processing the signal output from that system to enable the correct timing of the trigger pulses used to trigger electrical stimulating pulses at the stimulation signal generator 24 (or stimulation signal generators if a plurality of them are present). In addition the signal processor can be designed to deliver trigger pulses in the millivolt range whereas the stimulation signal generator delivers electrical stimulating pulses with a substantially higher amplitude, say up to 50 volts.

Figure 2:
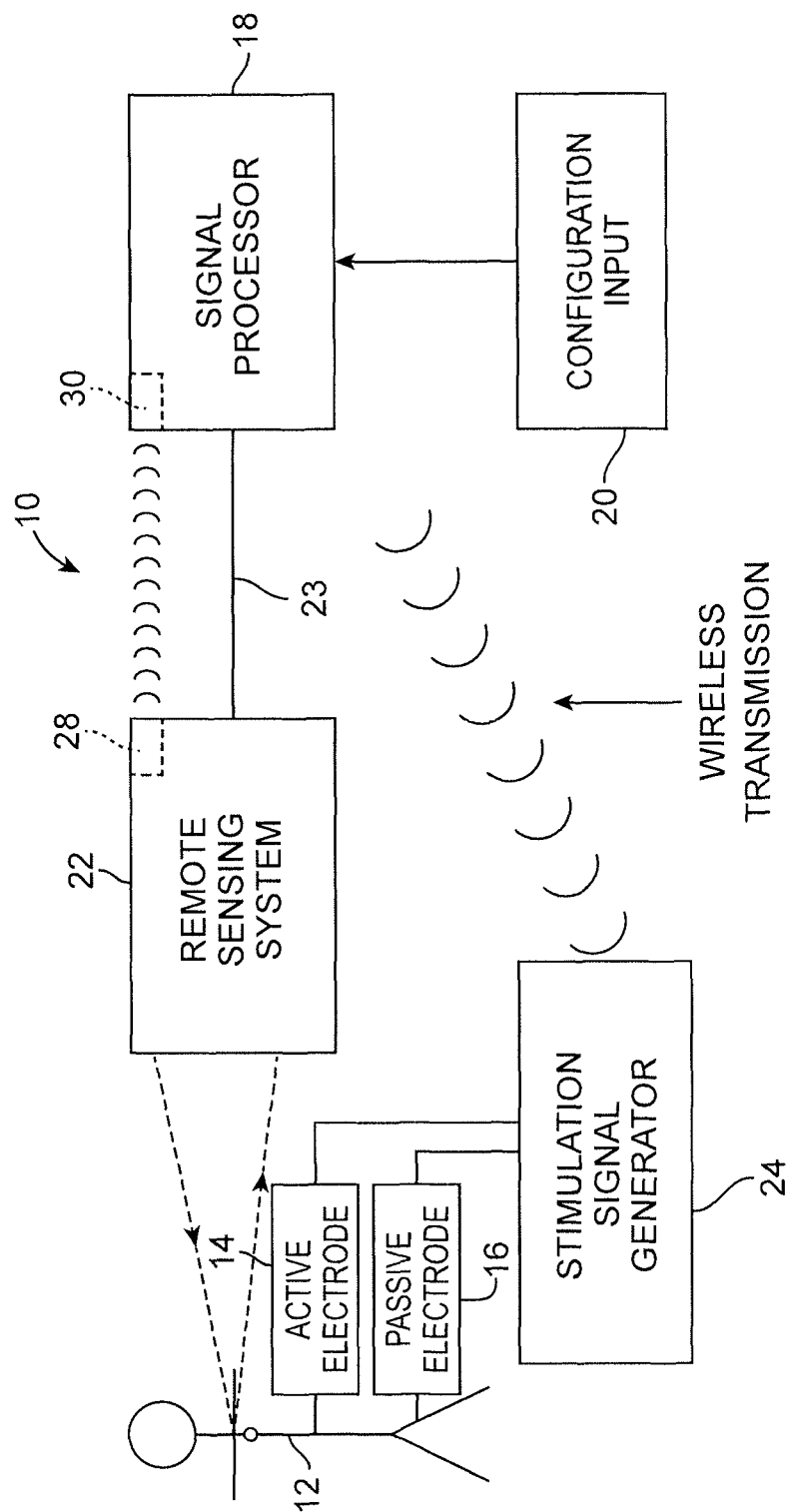
FIG. 2 is a diagram similar to FIG. 1 of a second embodiment of the present invention.

A large number of different variants of the above described basic apparatus can be realized. For example, as indicated in FIG. 2, when a remote sensing system 22 is provided, the signal processor 18 can be integrated into said remote sensing system 22 or connected to it by a lead 23. The communication between the remote sensing system 22 and the signal processor could, however, also take place via a transmitter 28 and a receiver 30 as indicated in dotted lines in FIG. 2.

Because remote sensing systems are not yet well developed it is however preferred to use a sensing system 22 which is attached to the patient and it is then preferred for said sensing system 22 to be adapted for wireless transmission of said heart information to the signal processor 18. This can be achieved by a wireless transmitter 28 embodied in or associated with the sensing system 22 and an antenna 30 embodied in or associated with the signal processor 18, as shown in FIG. 1.

Figure 3:
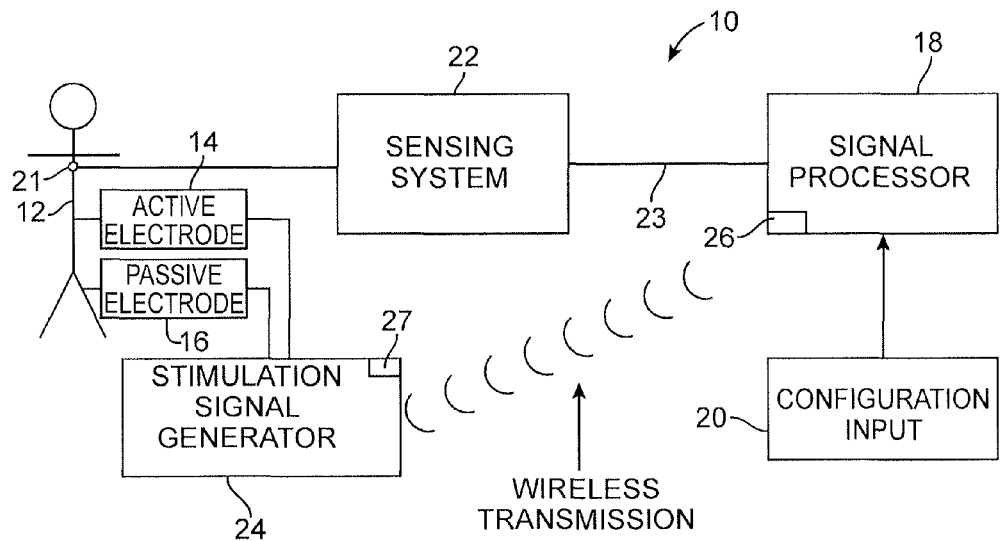
FIG. 3 is a further diagram similar to FIG. 1 of a third embodiment of the present invention.
Figure 3A:
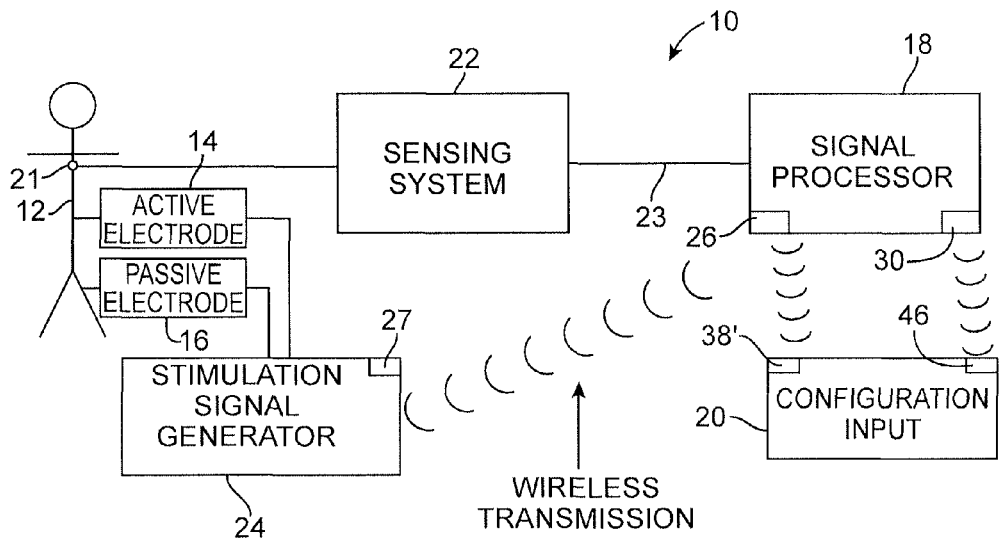
FIG. 3A is a diagram related to that of FIG. 3 but showing bidirectional wireless communication between a configuration input for a signal processor and the signal processor.

However, as indicated in FIG. 3, even if a sensing system or unit 22 is used which is attached to the patient, i.e. is not a remote sensing unit, the signal processor 18 could still be integrated into the sensing system or connected to it by a lead 23. Another possibility, which could be used in all embodiments and which is shown in FIG. 3A, is for the signal processor 18 to be adapted to receive at the receiver 30 configuration information transmitted to it from a transmitter 46 at the configuration input. As a further option, a receiver 38' can be provided at the configuration input, e.g. to receive information from the signal processor 18 or from a medical evaluation unit. This has the advantage that the configuration input 20 can, for example, include a keyboard and a display screen of useful size which is present at a location remote from the signal processor which is carried by the patient, so that the patient is free to move unencumbered by the keyboard and screen. The wireless connection between the configuration input 20 and the signal processor 18 and/or between the configuration input 20 and the medical evaluation unit 32 can be realized by a mobile phone, a personal digital assistant with phone function, or any device with transmitter and/or receiver capabilities, or any standard piece of equipment having a transceiver, a microprocessor, a memory for storing software and data, a battery, or other source of power and a clock.

Figure 4:
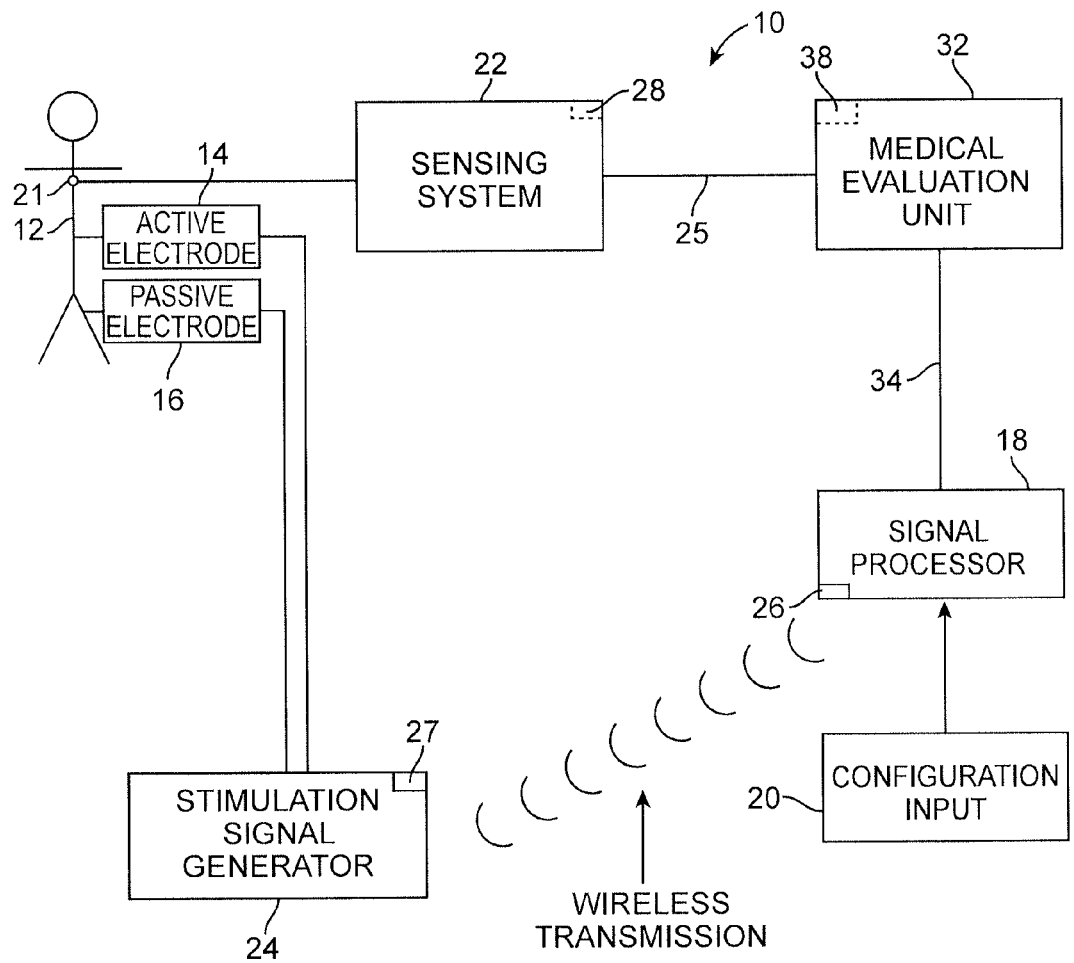
FIG. 4 is a fourth diagram similar to FIG. 1 showing a fourth embodiment of the present invention.

It can also be beneficial if in accordance with FIG. 4, the sensing system is adapted to transmit said heart information to a medical evaluation unit 32 and the medical evaluation unit 32 is adapted to transmit signal configuration information to said signal processor 18, with the signal processor 18 taking account of said configuration information when generating the control signal information.

The medical evaluation unit can be a computer, e.g. a suitably programmed PC, or can take the form of an information presentation system viewed by a skilled operator who then provides input information to the signal processor—e.g., via the configuration input 20, or directly via an input at the medical evaluation unit which passes via the lead 34 to the signal processor 18—to ensure the appropriate stimulation signals are triggered at the stimulation signal generator.

The configuration input 20 is adapted to input all parameters to the signal processor 18 which are necessary for it to generate the required operating or trigger signals for the stimulation signal generator(s) 24. The medical evaluation unit, which can be connected to the configuration input 20 (or communicate with it wirelessly), may well have a need to check the operating data currently input at the configuration input 20, and thus the configuration unit 20 is designed to make the required information available to or accessible by the medical evaluation unit 32. Equally, it may be useful for the signal processor 18 to not only receive operating parameters from the configuration input 20 (or from the medical evaluation unit 32) but for the actual operating parameters being used by the signal processor to be available to or accessible by the configuration input 20 and/or the medical evaluation unit 32, so that transmission of said operating data from the signal processor 18 to the configuration unit 20 and/or to the medical evaluation unit 32 is also preferably provided for.

More specifically, the medical evaluation unit 32 is adapted to display and/or print out the signals from the sensing system, e.g. in the form of an electrocardiogram, or simply in the form of a succession of R-R peaks possibly together with entries showing the positions of the T-waves or the predicted ends of the T-waves, together with signals representative of the applied stimulation. This enables a skilled operator viewing the display to control the signal processor, either by signals input by him at the medical evaluation unit or at the signal processor (optionally at the configuration input or another dedicated input) to change the stimulation treatment applied to the patient. If the medical evaluation unit 32 is realized as a computer or includes a microprocessor—which will normally be the case—then it is preferably programmed to control the signal processor to generate trigger signals for triggering the stimulation signal generator(s) to apply the appropriate stimulation signals to the patient. The position at which the control signals from the medical evaluation unit enter the signal processor can also be considered to be a configuration input.

In the example of FIG. 4 a non-remote sensing system 22 is used, i.e. one attached to the patient and signals from the sensing system 22 are transmitted by a lead 25 to the medical evaluation unit 32. As mentioned the medical evaluation unit 32 is connected via a lead 34 to the signal processor 18. As before, the signal processor 18 transmits the timing signals for the electrical stimulation pulses via the transmitter 26 to the receiver 27 at the stimulation signal generator.

Figure 5:
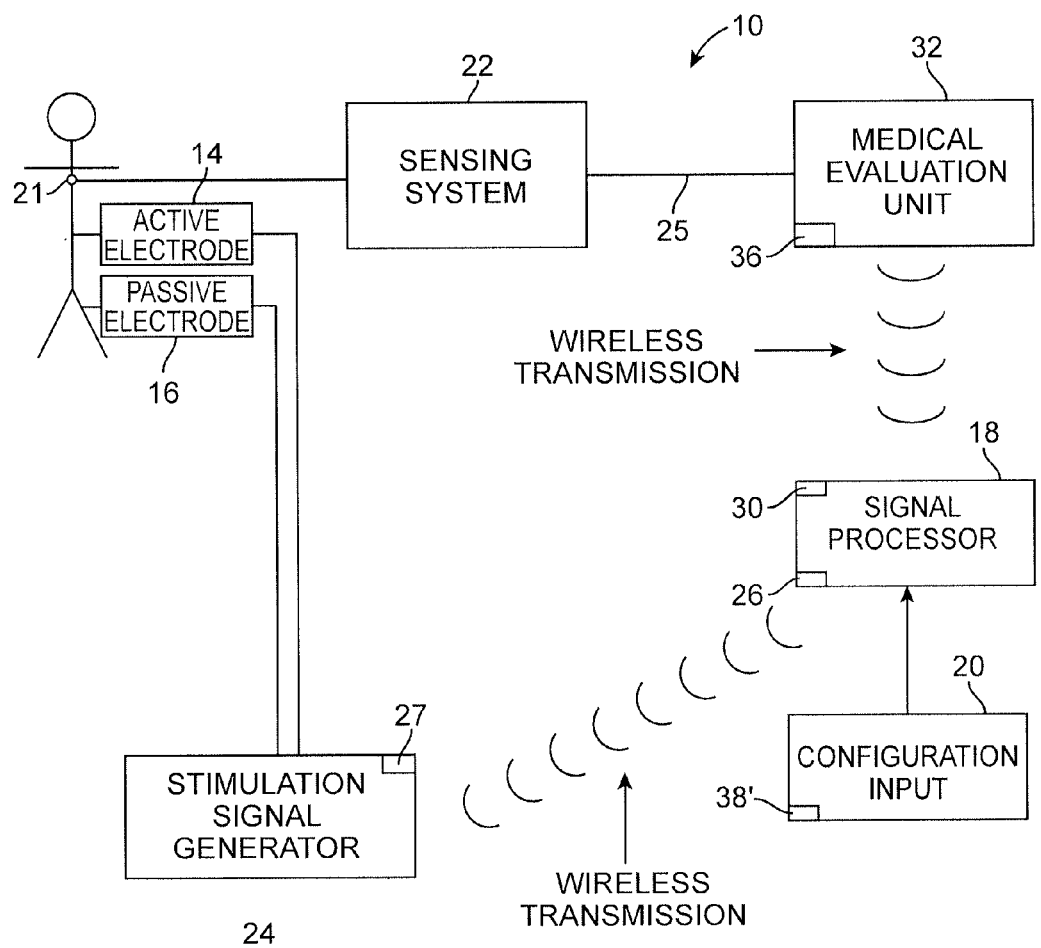
FIG. 5 is a schematic diagram similar to FIG. 4 showing a possible alternative version of the embodiment of the FIG. 4.
Figure 6:
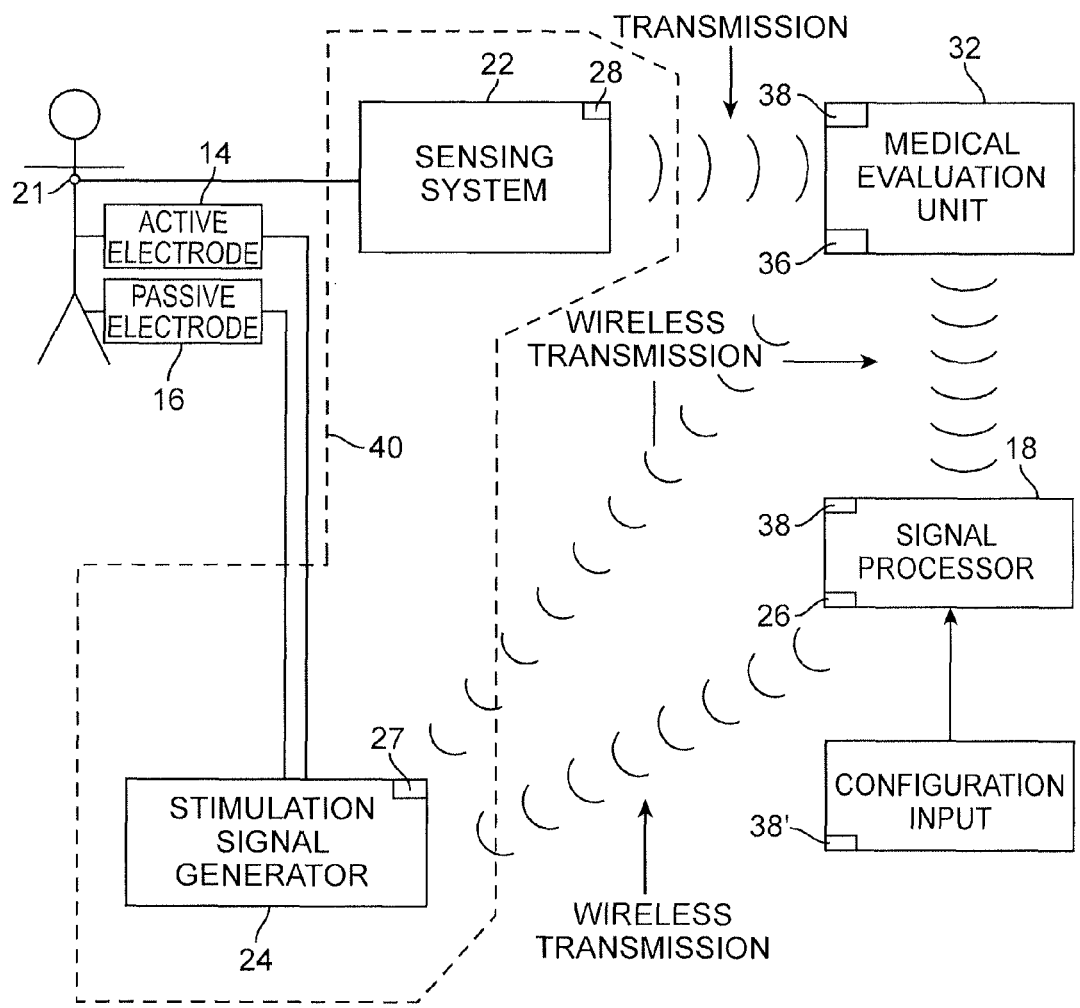
FIG. 6 is a further diagram similar to FIG. 4 showing a yet further alternative embodiment of the present invention

It is, however, preferable for the medical evaluation unit 32 to be adapted for wireless transmission of said configuration information to said signal processor 18 as shown in FIG. 5. This can be done by means of a transmitter 36 at the medical evaluation unit which communicates with a receiver 30 at the signal processor or a receiver 38' at the configuration input 20. In an alternative (not shown) the receiver 30 can be integrated with the transmitter 26 and configured as a transceiver. This arrangement enables the medical evaluation unit and the signal processor to be housed in different rooms and indeed at completely separate remote locations. For example, the medical evaluation unit could be located in a special facility in a hospital and the signal processor in a doctor's practice in a different building, town or country. It is particularly preferable if, as shown in FIG. 6, the sensing system is adapted to transmit said heart information to said medical evaluation unit by wireless transmission. For this purpose the sensing system 22 has a transmitter 28 and the medical evaluation unit a receiver 38.

This variant has the advantage that the patient can be completely mobile and located a considerable distance from both the medical evaluation unit 32 and the signal processor 18. The patient only needs to carry on his person the sensing system 22 with transmitter 28 and the stimulation signal generator(s) 24 with receiver 27. Both the sensing system (22) and the stimulation signal generator(s) 24 can be made very small, so that the patient's mobility is not hindered and he can be subjected to long-term treatment while going about his daily life. In the variant shown in FIG. 6 the receiver 38 and the transmitter 36 at the medical evaluation unit can be combined into a transceiver. Even if the patient carries the signal processor 18 in the form of a mobile phone on his person, which is one possibility, this does not hinder him unduly because he is not wired to the phone.

It would also be possible to combine the signal transmitter 28 at the sensing system 22 and the signal receiver 27 at the stimulation signal generator 24 into a single transceiver. Moreover, the stimulation signal generator and the sensing system could be integrated into a single device as indicated by the dotted outline 40 in FIG. 6.

One particularly favorable realization of such a single device would be a dedicated unit which would, for example, take the form of a mobile phone, a personal digital assistant with phone function or any standard piece of equipment having a transceiver, a microprocessor, a memory for storing software and data, a battery or other source of power, a clock and the necessary interface(s) for connection to the sensor or sensors 21 at the patient, such as ECG sensors, and to active and passive electrodes 14, 16. The dedicated unit could also include a screen for displaying a trace symbolizing and relating to the positions of the R-R peaks and the end of the T-wave and possibly a signal relating to the stimulation applied. The realization as a mobile phone is particularly attractive since a mobile phone has all the necessary elements of the dedicated unit, or could be provided with additional interfaces if necessary. In particular a mobile phone has plenty of storage capacity for storing software and data relating to the additional functions it has to perform for implementing the present teaching. Indeed it could be further developed to function as a heart monitor and provide timely warnings to a receiver at, e.g., the medical evaluation unit, if a heart attack is incipient—enabling remedial action to be taken at an early stage, e.g. in a telephone call from an operator at the medical evaluation unit to the patient concerned, or by alerting an emergency service.

Moreover, the signal processor 18 can also take the form of a dedicated unit which could, for example, take the form of a mobile phone, a personal digital assistant with phone function or any standard piece of equipment having a transceiver, a microprocessor, a memory for storing software and data, a battery or other source of power, a clock and an input for configuration data and/or control signal information. It could also comprise a mobile phone related unit having one or more signal receivers, transmitters in addition to a telephone aerial or aerials.

Figure 7:
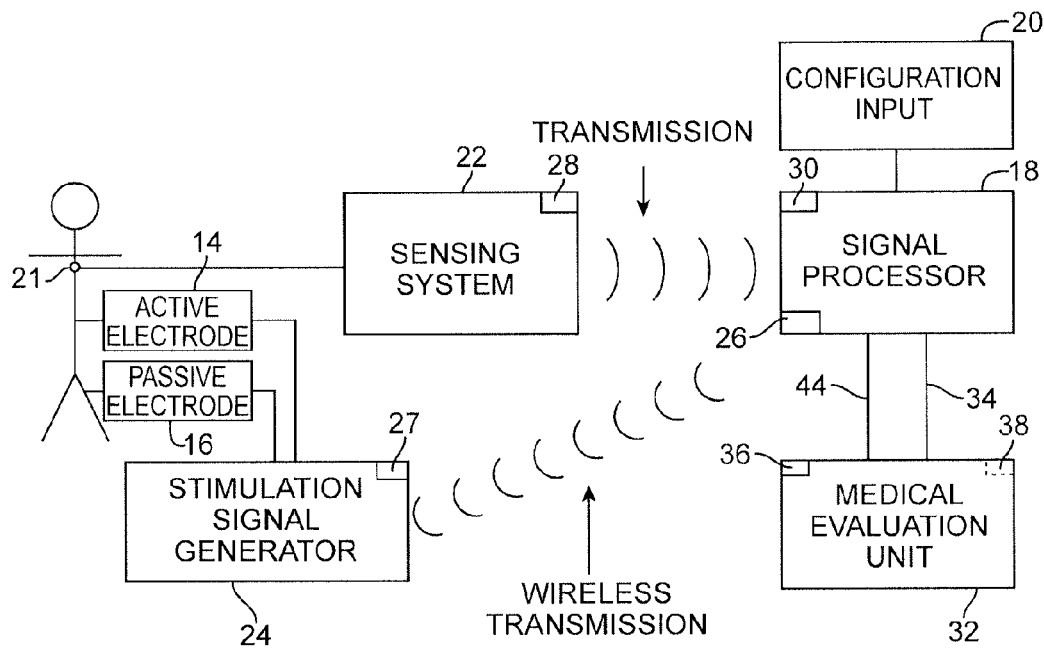
FIG. 7 is a further schematic diagram related to FIG. 4 but showing a yet further embodiment of the present invention.

In another variant shown in FIG. 7 the sensing system 22 transmits heart signal information to the signal processor 18 and the signal processor is adapted to transmit or relay heart information to the medical evaluation unit 32 via a lead 44 and said medical evaluation unit is adapted to transmit signal configuration information to said signal processor via the lead 34. The signal processor 18 then takes account of the configuration information when generating said signal information.

Figure 7A:
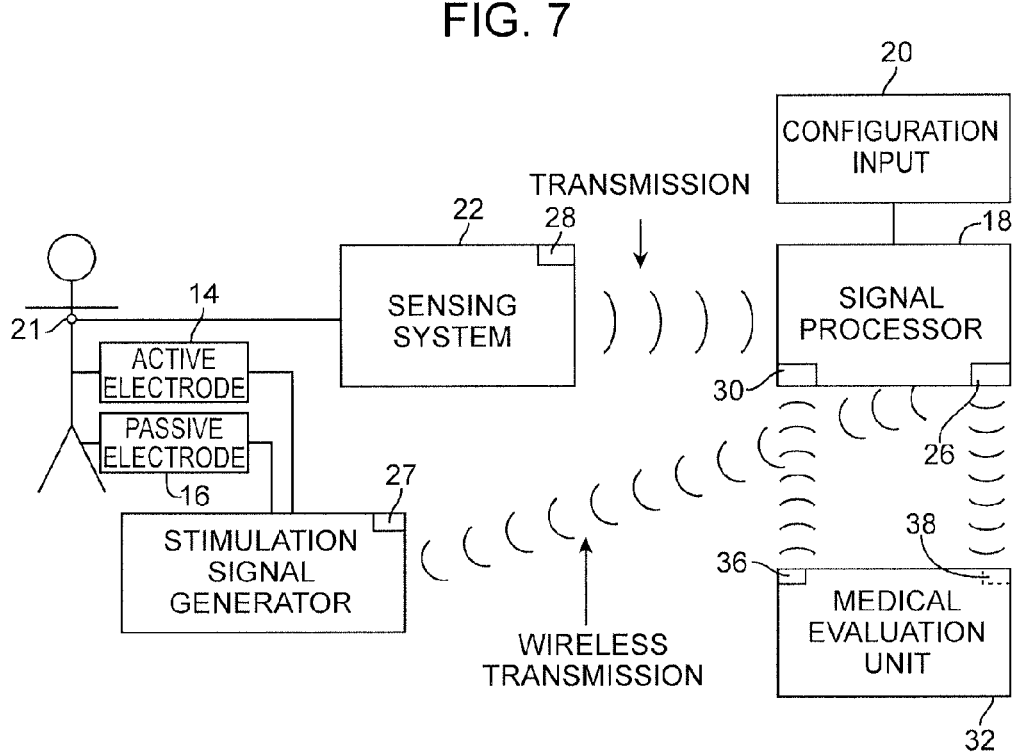
FIG. 7A is a diagram related to that of FIG. 7 but showing the possibility of bidirectional wireless transmission between a medical evaluation unit and a signal processor.

In an alternative shown in more detail in FIG. 7A the signal processor 18 is adapted to transmit said heart information to said medical evaluation unit 32 by wireless transmission as indicated by the receiver 38 shown in dotted lines at the medical evaluation unit and the medical evaluation unit 32 is adapted for wireless transmission of said configuration information via the transmitter 36 to the receiver 30 at the signal processor 18. In this case the receiver 30 and the transmitter 26 can form one transceiver and the receiver 38 and the transmitter 36 can form a second transceiver. Again the transmitter 28 and the receiver 27 can also be combined into a transceiver and all transceivers can be realized as a mobile phone or as a mobile phone related unit.

Figure 7B:
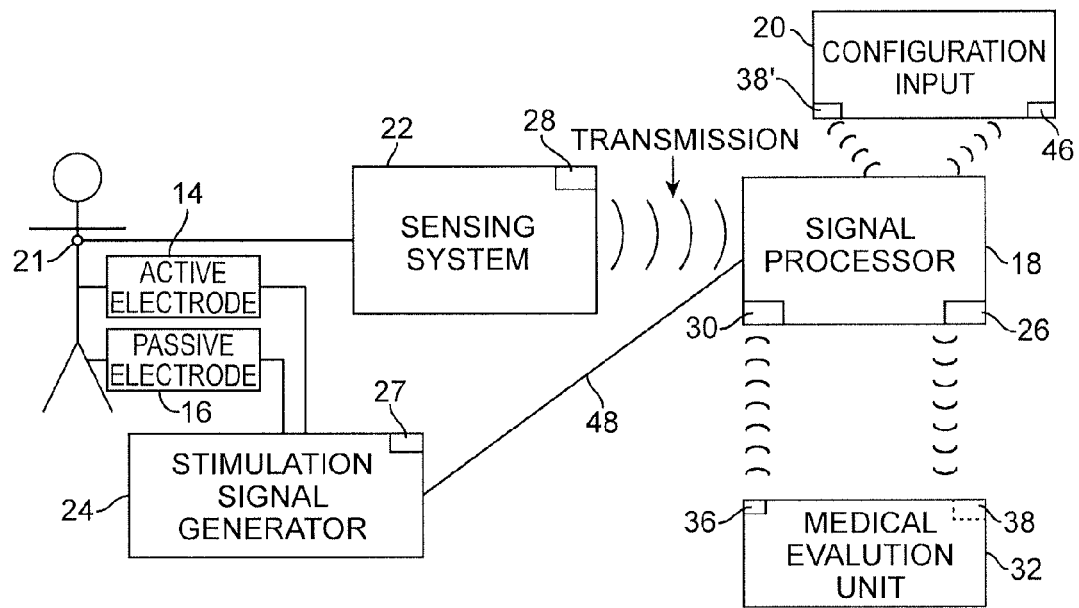
FIG. 7B is a diagram similar to FIG. 7A but showing the signal processor connected by a lead to or integrated with a stimulation signal generator.

FIG. 7B shows possible further modifications of the embodiment of FIG. 7A. In one modification the configuration input 20 communicates with the signal processor 18 by wireless transmission, as discussed in connection with FIG. 3A and/or with the medical evaluation unit 32 by wireless transmission. For example, the transmitter 46 at the configuration input 20 can communicate with the receiver 30 at the signal processor 18 and/or with the receiver 38 at the medical evaluation unit 32. Moreover, the transmitter 26 at the signal processor can transmit information to the receiver 38' at the configuration input 20. The receiver 38' at the configuration input can alternatively or additionally receive information from the medical evaluation unit by wireless transmission from the transmitter 36 provided at the medical evaluation unit 32. For example, the medical evaluation unit could reset the parameters of the stimulation being applied to the patient by sending new configuration data either directly to the signal processor 18 or via the configuration input 20 and could also send a message to the configuration input 20 advising the patient of the changed parameters when he views or switches on the screen associated with the configuration input 20.

Furthermore, FIG. 7B shows by way of the line 48 that the signal processor could also be connected by a lead to the stimulation signal generator(s) 24. If a plurality of stimulation signal generators 24 are present, then the signal processor 18 could be connected to one or more of them by a lead and the other signal generators could either be interconnected by leads or communicate with each other wirelessly.

In a further alternative the signal processor could be integrated with all or one of the stimulation signal generators 24 and could communicate wirelessly with each stimulation signal generator 24. In these cases, i.e. when the signal processor is connected by a lead to one or more stimulation generators 24 or is integrated with one or more of them, the signal processor 18 is physically carried by the patient. This is not a problem because the signal processor 18 can be made very small and requires little power to drive it. This power can readily be supplied by the battery associated with each stimulation signal generator. It is later described with reference to FIGS. 14A and 14B how a stimulation signal generator can be used for each pair of active and passive electrode 14, 16 and can, for example, be clipped to them. It is entirely possible and indeed sensible to integrate the signal processor 18 into one of the stimulation signal generators 24 or possibly to have a signal processor 18 integrated into each of the stimulation signal generators 24. This would make it possible to use one standard integrated component (stimulation signal generator+signal processor) for each pair of electrodes with economy of scale due to the need to manufacture only one standardized device. Moreover, since each stimulation signal generator has its own battery, the individual batteries can be kept relatively small and the distributed weight is not a problem for the patient.

In addition, it should be noted that the embodiment of FIG. 3A can also be modified to include a medical evaluation unit 32 communicating with one or both of the configuration input

20 and the signal processor 18 by wireless transmission (optionally bidirectional as discussed in connection with FIG. 7B).

As mentioned above one of the objects of the present invention is to improve the design of the stimulation signal generator to make it lighter, compacter and to improve the working life of the batteries that are used. One way of achieving this is to avoid a bulky and heavy transformer for the power circuit.

Figure 8:
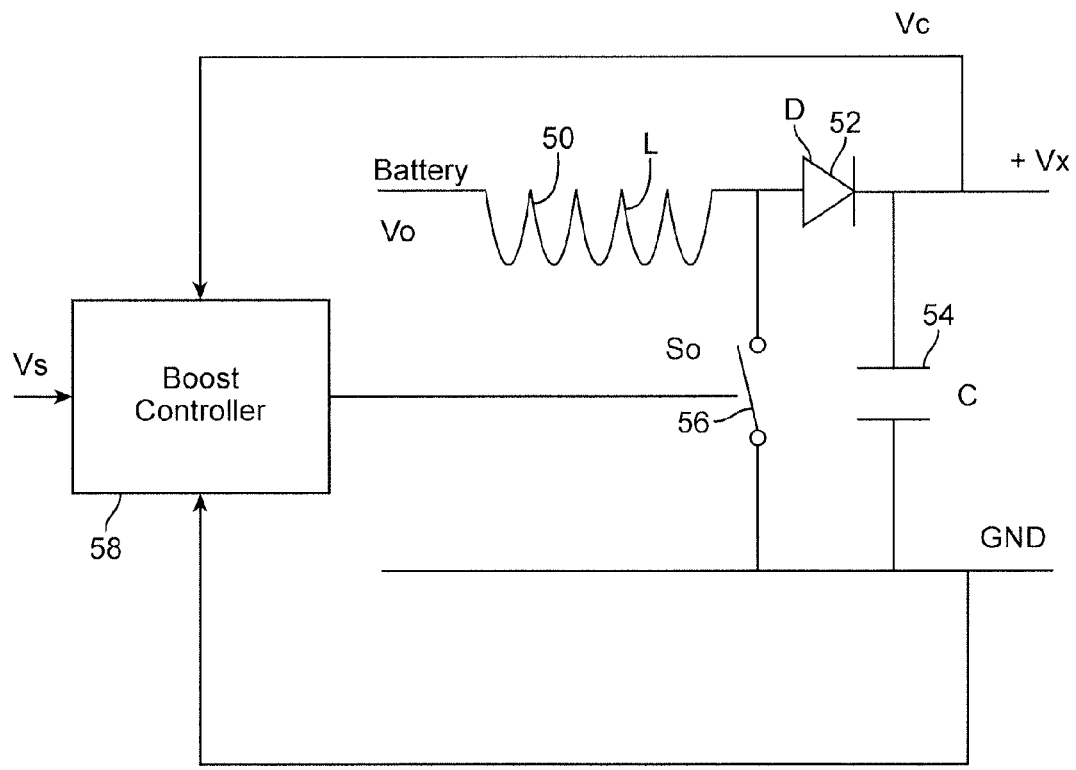
FIG. 8 is a schematic diagram showing a first embodiment of a boost converter capable of use for the present invention to increase the output voltage of a battery to a higher voltage for electro stimulation purposes.
Figure 9:
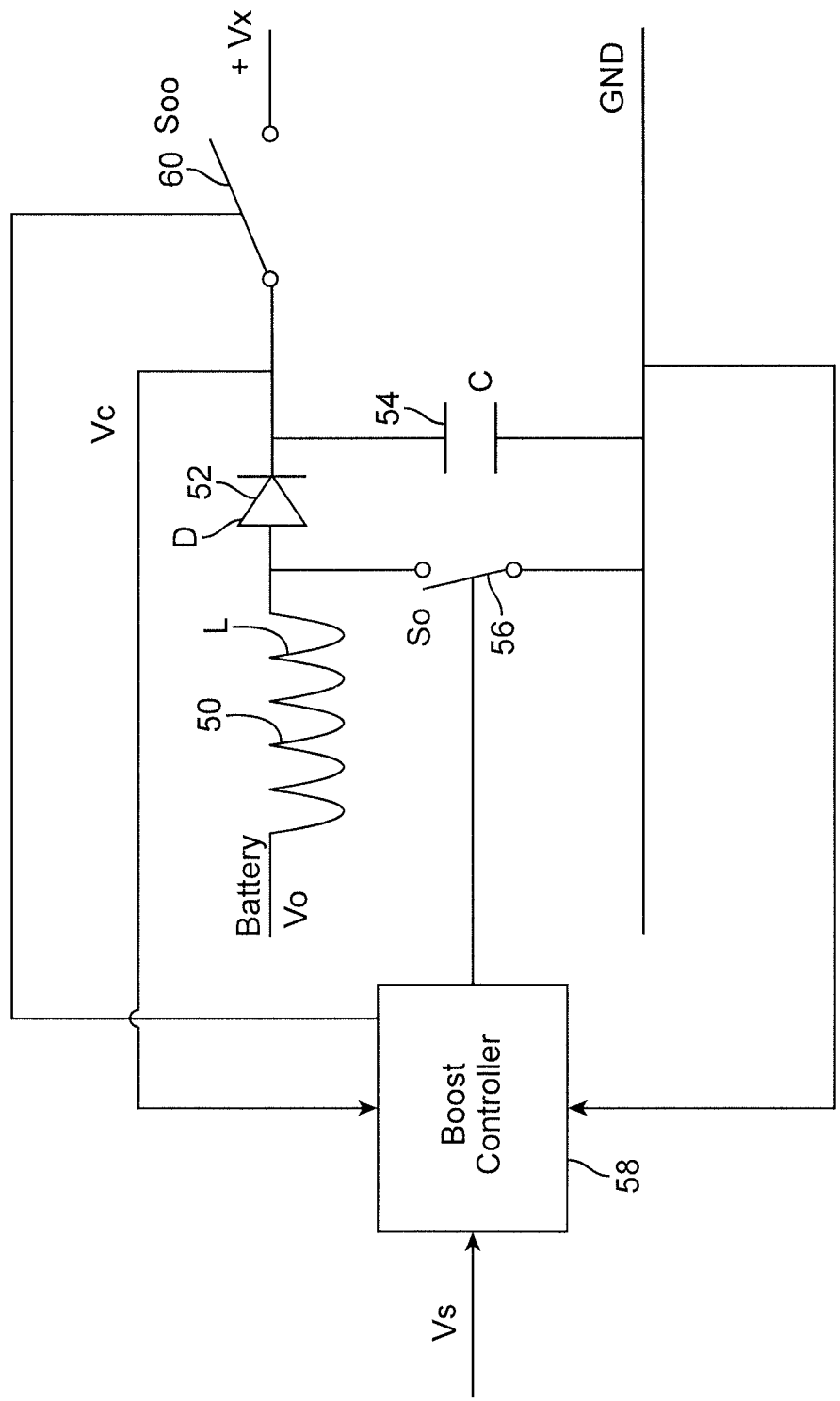
FIG. 9 is a schematic diagram of a second boost converter similar to that of FIG. 8 but further modified for the purposes of the present invention.

The reasoning behind the concept is as follows: At low battery voltage Vo and at a given maximum stimulation end voltage Vmax of a power circuit, the transformer can become too bulky and too heavy, because the ratio of the transformer would have to be increased to reach Vmax, the more Vo is being reduced. As an example: at Vo=7.4 V and at Vmax=45 V, a standard transformer ratio of, e.g., 1:10 can be used by increasing the output voltage from 5 V to 50 V, allowing Vmax of 45 V without distortion. At Vo of 1.2 V a ratio of 1:50 would have to be used to increase the output voltage from 1.0 V to 50 V, allowing Vmax of 45 V without distortion. Such a transformer would be inordinately heavy. The basic solution provided by the present invention is to use a boost converter which is shown in FIG. 8. It consists of an inductor 50 "L", a diode 52 "D", a capacitor 54 "C", a switching component 56 "So" and a boost controller 58. In an improved version of the boost converter a second switching component 60 "Soo" shown in FIG. 9 is used which is connected to the battery voltage supply Vo, and to ground, GND. The complete circuit shown in FIG. 10 further involves a switching set up, e.g., the form of a so-called H-Bridge involving the switches S1, S2, S3, S4, is connected to the two outlets (+Vx and GND) to allow the desired switching to be controlled by an H-Bridge controller. In integrated circuits, the voltage Vo from the battery is nowadays typically equal to 1.2 V.

Any switching component can be used for the switches So, Soo, S1, S2, S3 and S4, such as electronic analog switches, transistors, triacs, etc., whatever is best suited for micro integration to keep dimensions small. There are many ways how such a booster converter can be switched. The following describes one specific example. The description below shows, as a preferred example, how a desired constant voltage signal, a fully balanced plus/minus signal as shown in the impulse diagram of FIG. 11, can be achieved to be applied to a patient using a booster converter.

Figures 11A, 11B:
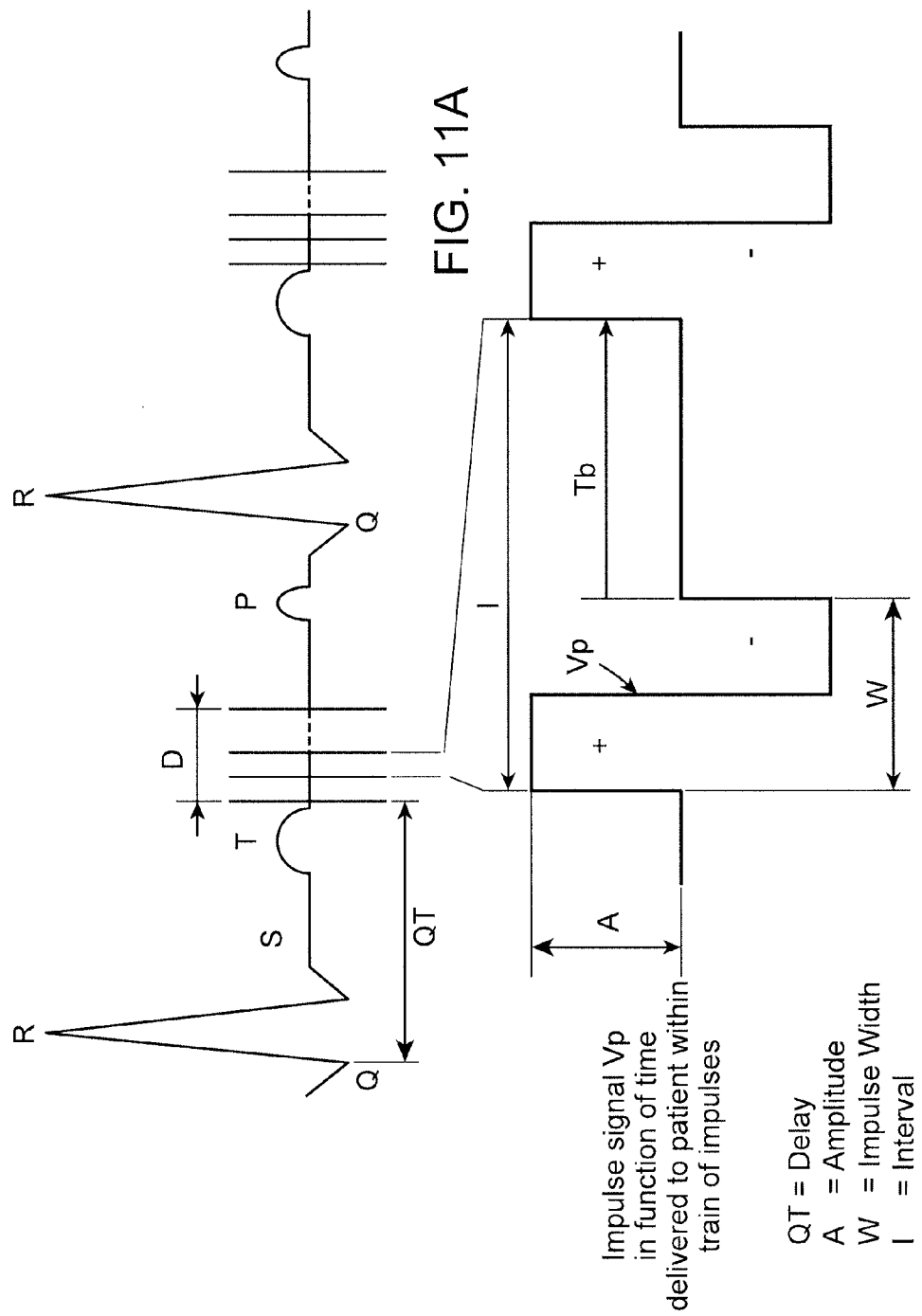
FIG. 11A is a schematic diagram representing an ECG trace taken from a patient with electrical stimulation pulses superimposed thereon, this being a diagram which can be displayed at the sensing system, at a medical evaluation unit associated with the sensing system or at a signal processor associated with the sensing system.
FIG. 11B is a diagram showing an enlarged scale the shape of two sequential biphasic pulses of the electro stimulation pulses shown in FIG. 11A.

The diagram of FIG. 11 shows in FIG. 11A a typical e.c.g. trace with the repeating signal elements QRSTPQR . . . as well known to any cardiologist. Superimposed on this trace and starting at the end of the T-wave; i.e. after the time QT in FIG. 11A is a stimulation signal comprising a first train of pulses having a duration D with two sequential pulses of this train (which are representative of all the pulses) being shown to an enlarged scale in FIG. 11B. it is noted that the relative amplitudes of the pulses in FIG. 11A are to different scales. In practice the amplitude of the stimulation pulses during the interval D is in the range up to ±45 volts whereas the peak amplitudes of the R-peaks are of the order of millivolts.

The graph of FIG. 11B shows how the impulse signal Vp varies as a function of time (with time being shown to an expanded scale relative to FIG. 11A). The pulses of FIG. 11B are so-called biphasic pulses. That is to say the impulse signal Vp increases from zero to a maximum with a relatively sharp rise time, dwells at the peak amplitude for a time essentially equal to W/2, then drops sharply to a minimum value at which it persists for a further time equal to W/2 following which it returns to zero and remains at this level for a period Tb prior to repeating again. Thus, the desired biphasic signal is essentially a rectangular wave signal with positive and negative components of balanced amplitude, with the pulses having a duration W shorter than the pulse interval Tb. This signal results in a minimum net electrical loading of the patient and a minimum net consumption of energy to achieve a particular muscle contraction and maintain it for a period of time which is actually greater than D and up to two to three times the duration D. Particularly preferred excitation signals are described in WO2005/044374.

Figure 12:
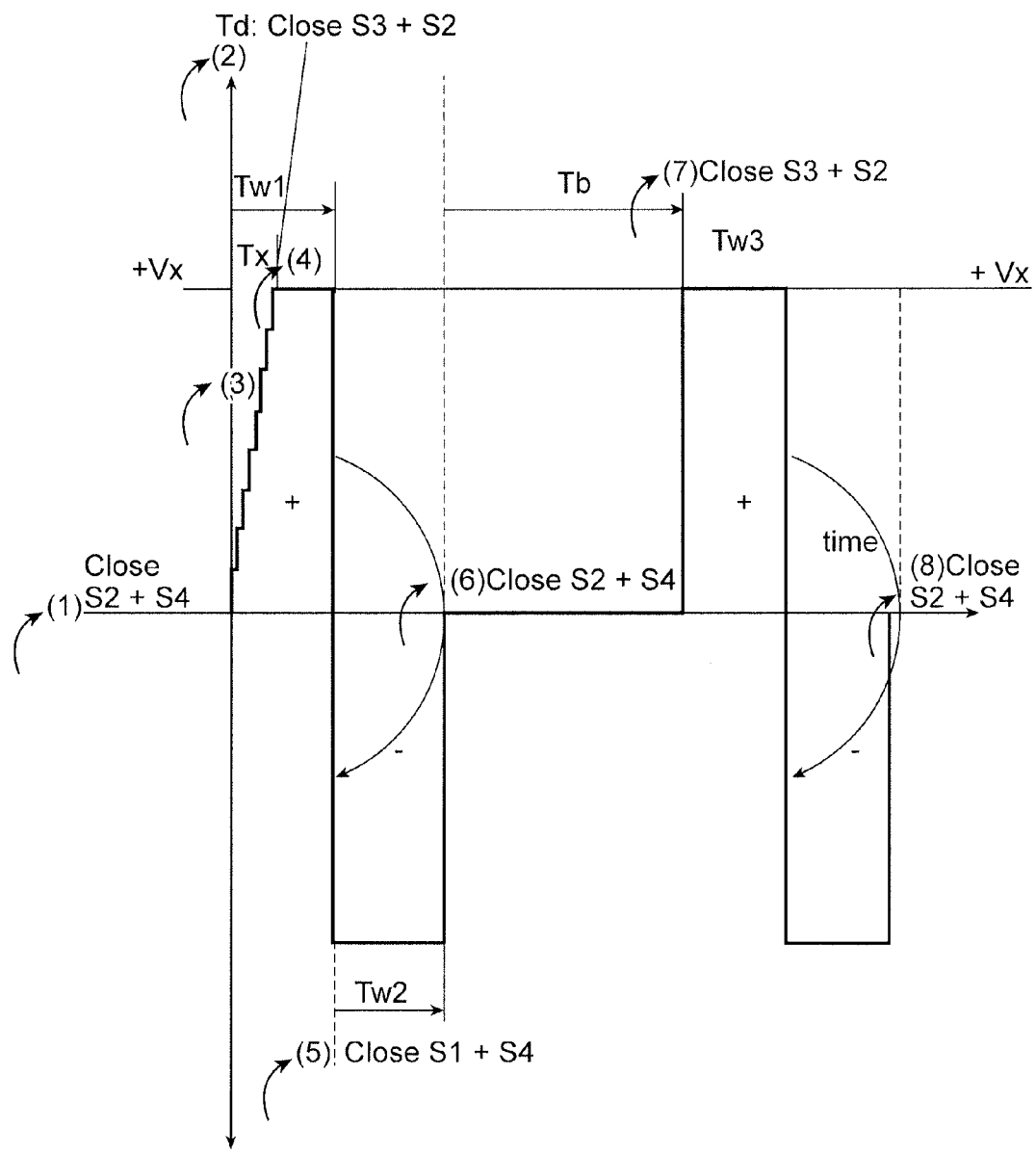
FIG. 12 is a schematic diagram explaining the operation of the boost converter of FIG. 8.

To achieve the positive constant voltage flank of FIG. 11B using the circuit of FIG. 8 the switching component So is switched continuously by the boost controller to build up in small digital steps to the desired maximum voltage V as shown in FIG. 12 as one of the parameters set by the controller to the signal generator and thus to the boost controller in order to regulate the desired constant output voltage +Vx, for the duration D of the package of impulse trains, see the impulse diagram of FIG. 11A. For this purpose the boost controller has a feedback of the effective voltage Vc of the capacitor C from the positive output compared to ground "GND" so it can regulate the value Vx to become and stay constant at the set value Vs. The boost controller uses a clock (not shown) to open and close the switching component So at high frequency.

Initially, the H-Bridge controller closes switches S2+S4 (S1+S3 are open). The active and passive electrodes (14, 16) are connected to GND and Vp on the patient=0 V. At the desired time Td (2), the controller closes switch S3+S2 (S1+S4 are open). As a consequence +Vx is connected to the active electrode 14 on the patient and the GND is connected to the passive electrode 16 on the patient. A current corresponding to the actually prevailing voltage difference Vp and the resistance and capacitor value of the human body flows between the electrodes.

Because the switch So is continuously closed and opened and closed and opened at the frequency determined by the boost controller, and because the diode D prevents current flowing back, the capacitor is charged and increased in its voltage each time the switch So is opened and, as a consequence, the voltage on the patient Vp is incrementally increased (3) until after time Tx the set voltage Vs is equal to the voltage Vx, so the voltage on the patient now has become Vp=+Vx (4). The voltage gradient increase is proportional in time to the frequency of the switching of So and the voltage steps are proportional to the selected steps. Typically, a 1 MHz boost controller 58 could e.g., boost the voltage from 0 V to 50 V in 20 steps per volt, each requiring one switching step in the time Tx of 1 milliseconds (50 V times 20 steps/V=1000 steps; 1000 steps divided by 1'000'000 steps/sec=0.001 sec or 1 millisecond.

The switching component So continues to be switched with S3+S2 being closed (S1+S4 are open) to recharge the capacitor in order to compensate the current flowing to the patient. The voltage +Vx=Vp is applied to the active electrode 14 of the patient and the corresponding current flows for the desired time Tw.

To achieve the negative constant voltage flank at the desired time Tw1 (5), the H-Bridge controller switches instantly and closes S1+S4 (S3+S2 are now open): Now the active electrode 14 on the patient is connected to GND and the passive electrode 16 becomes −Vx, because the voltage Vc on the capacitor cannot jump. The voltage on the patient Vp is now the negative voltage −Vx and a corresponding current now flows from the passive electrode to the active electrode. This inversion of the voltage +Vx at the output of the boost converter is indicated in FIG. 12 by the dotted line. The diagram shows that the output of the boost converter always stays at the constant level +Vx, however it is the switching of the H-Bridge, which reverses the effect Vp on the patient. The boost controller continues switching the switch So and the negative voltage −Vx is being kept on the patient for a second period Tw2 (6). This is how an identical, but inverted (negative) signal can be produced simply by switching the H-Bridge correspondingly.

After period Tw2 has elapsed, the H-Bridge is now switches at point (6) and closes S2+S4 (S1+S3 are open). Now passive and the active electrodes 16, 14 are now again connected to GND and the human capacitor is discharged instantly and with this the voltage Vp on the patient drops immediately to zero. Switching of So can now either rest to save battery power or it continues to be switched and with this the capacitor keeps its charge for a break corresponding to the period Tb (7).

After the period of the break Tb (7) (the break is being calculated as the interval time I, minus impulse width W (see FIG. 11B) has elapsed, the H-Bridge controller switches closes switch S3+S2 (S+S4 are open). Now the charged capacitor can discharge instantly the positive voltage +Vx=Vp to the patient and the process described above resulting in positive and negative flanks is repeated.

After the period of the duration D has ended with a last switching of the H-bridge closing S2+S4 (8), hereby connecting both the active and passive electrode to GND and Vp=0, So switching can be stopped and the capacitor can either be discharged by closing S1+S2, for instant discharging of the capacitor, or alternatively, the capacitor maintains its charge until the next set value Vs defines whether the voltage has to be increased or decreased.

So for the next impulse of trains the process can be started again to design a constant voltage signal having the same or a different amplitude A. When the capacitor has not been discharged it can be boosted to the newly desired level (up or down).

Using such a boost converter and an H-Bridge any signal can be designed as a function of time at the outputs. The example described and shown is simply given as one possible example.

Figure 13:
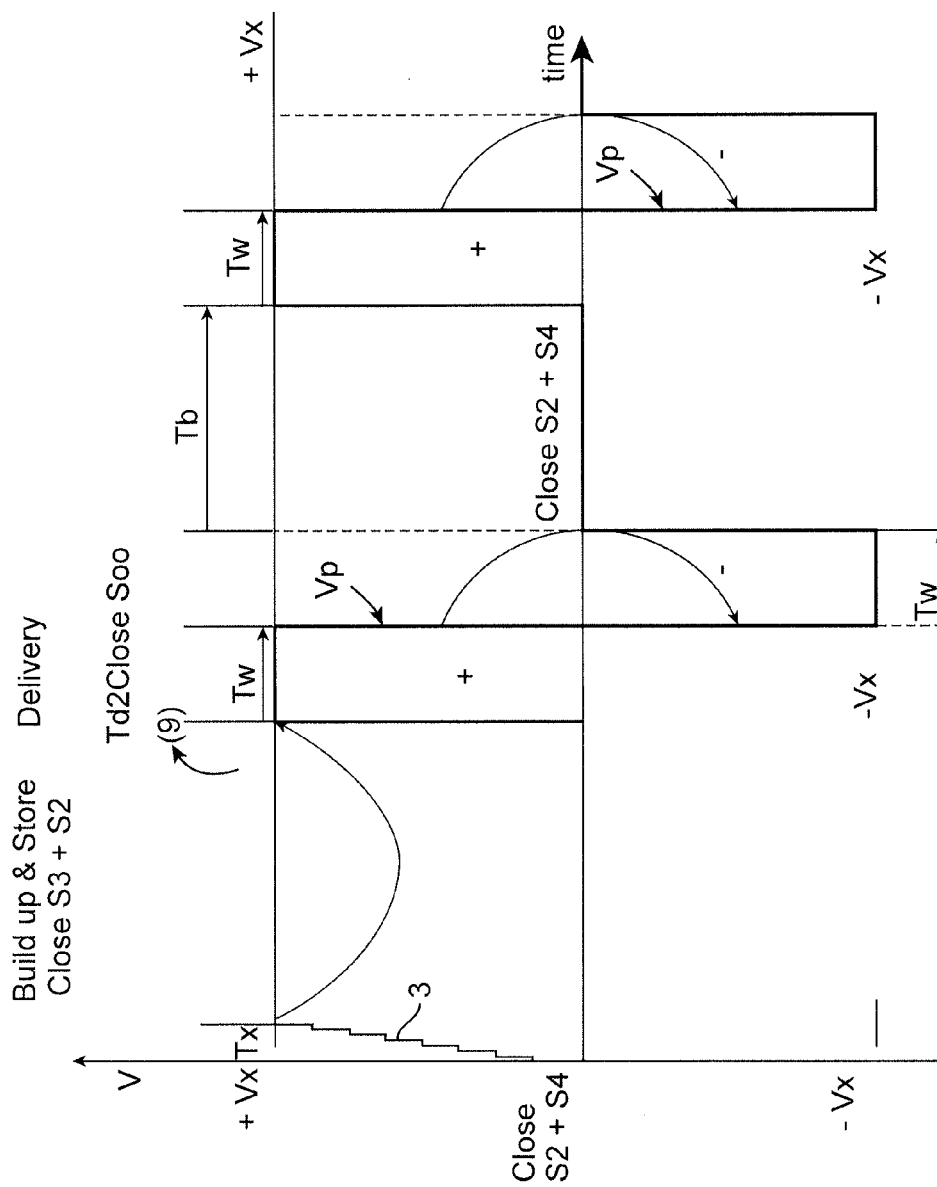
FIG. 13 is a schematic diagram explaining the operation of the boost converter of FIG. 9, FIGS. 14A and 14B are diagrams showing a simulation signal generator connected to a pair of active and passive stimulation electrodes suitable for use in any of the embodiments of the present invention, and indeed in a plan view (FIG. 14A) and in a side elevation (FIG. 14B)

The preferred embodiment of the boost converter and its operation will now be described with reference to FIGS. 9 and 13.

As noted above, the FIG. 9 embodiment includes an additional switching component Soo in comparison to FIG. 8 and this switching component Soo is provided and is also switched by the boost controller when required.

The setup works in principle in exactly the same manner as described with reference to the embodiment of FIG. 8, except that, for achieving the positive flank for the first time, the switch Soo of the positive booster converter is opened meaning that the designed positive flank of the voltage increase to Vx cannot be delivered to the active electrode 14 and the built up voltage Vx is stored in the capacitor. At the desired time Td2 (9), Soo is closed and the stored voltage Vx is instantly delivered to the active electrode, without the design-related delay Tx. The buildup of the desired voltage +Vx in the capacitor has to be done prior to the time Td−Tx to allow an instant delivery of the full voltage Vx.

All other steps remain the same as described with reference to FIGS. 8 and 12.

It remains to be said, that some effort is required to integrate switching component Soo into a micro integrated circuit, but there are ways how it can be done. Although the diagram of FIG. 13 is ideal, it is acceptable to use only the setup of FIG. 12 as an acceptable compromise.

As indicated above a plurality of pairs of active/passive electrodes 14, 16 are preferably provided and each pair of active/passive electrodes 14, 16 has its own stimulation signal generator 24 or power circuit 24 so that reference will be made here to multiple power circuits. Each power circuit of the multiple power circuits is placed directly onto a respective pair of active and passive electrodes, placed in the vicinity of each other onto the patient's skin avoiding the need for wiring between a power circuit unit and the electrodes. One terminal of each electrode is used to connect and carry the respective power circuit unit thus keeping the wiring to a minimum. Each stimulation signal generator 24 is equipped with switching components to form a so-called H-Bridge, S1-S4 and one boost converter is powered from a battery of a design voltage VO as described above with reference to FIG. 8 or FIG. 9.

The stimulation signal generator receives three different pieces of information. First of all it receives A) delay information, i.e. the exact moment when the power circuit has to stimulate relative to the heartbeat, from the signal processor 18 via the transmitter 26 of the signal processor and the receiver (RX) 27 of the stimulation signal generator B) parameters, i.e. combinations of amplitude, frequency, duration, signal width of single or multiple trains of stimulation packages from the data storage 60, where these parameters are stored. Such parameters are received via the receiver RX, whenever a corresponding new parameter is being sent by wireless communication from the signal processor 18. The delay information can also be stored in the memory or data storage 60 if it remains substantially constant and can be updated as required (depending e.g. on the patient's heart rate) from the signal processor 18.

C) the boost controller 58, having a clock (not shown), which controls the signal generator and the H-Bridge controller 64 in such a way, that they can deliver the wanted signal with the stored parameters at the correct delay time.

Thus, the receiver RX 27 receives from the transmitter 26 of the signal processor 18 addressed (coded) wireless information:
  a correct delay for each heartbeat,
  parameters whenever they have been changed, and
  sleep and wake up information in order to put the signal generator to sleep when not required in order to save battery power The stimulation signal generator 24 preferably includes a transmitter TX (which may be the transmitter 28 or could be a separate transmitter) can provide feedback information to the signal processor (e.g. via the receiver 30) such as:
  information on whether the stimulation signal generator is asleep or awake (ready to receive parameters)
  confirmation that a parameter change has been received and stored
  information on the remaining battery capacity etc.

Each power circuit unit (stimulation signal generator 24) has its own wireless communication means (antenna), common or separate for RX and TX (e.g. 27, 28), depending on the means of wireless communication.

Figure 10:
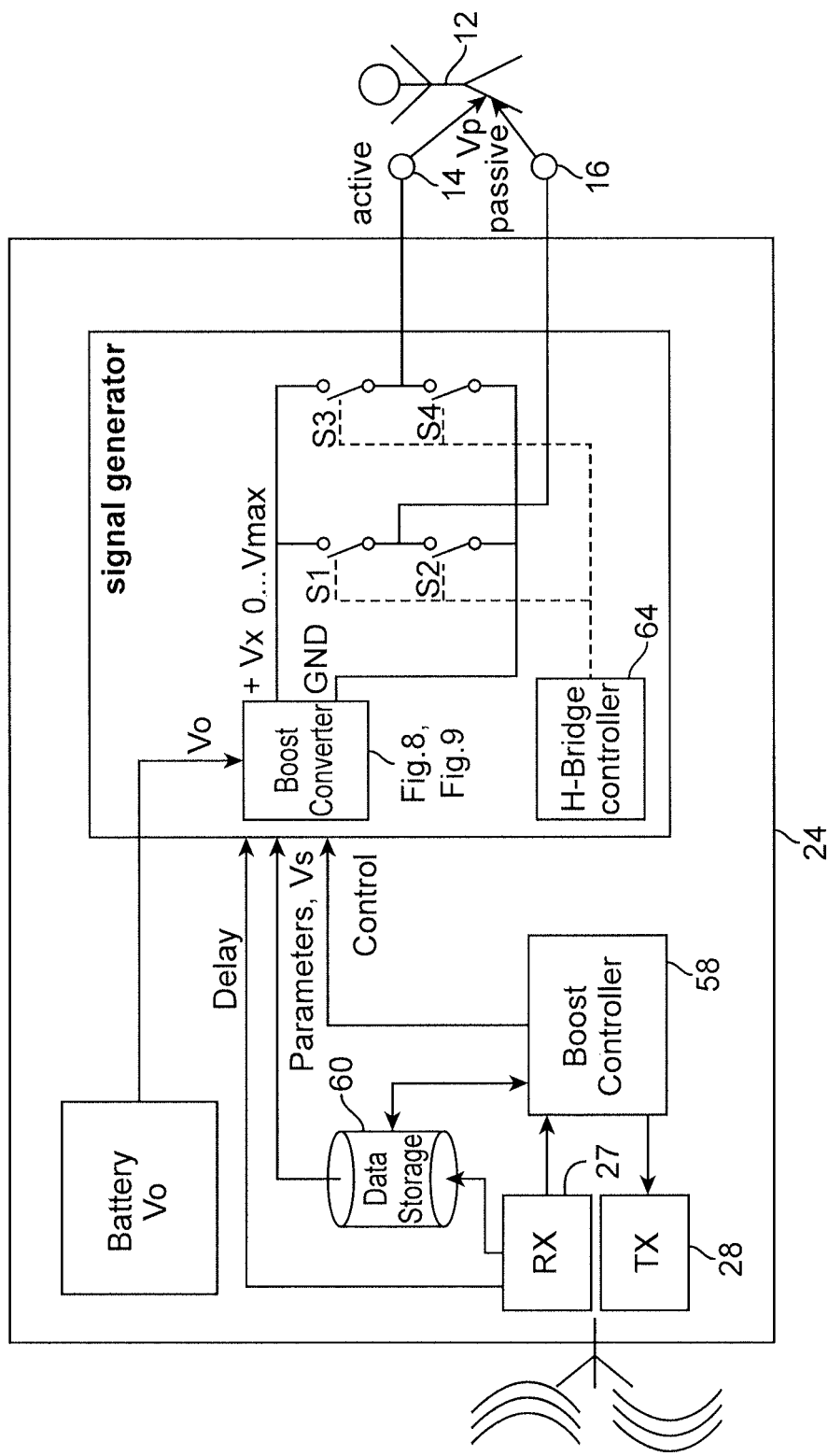
FIG. 10 is a schematic diagram of a stimulation signal generator useful for the present invention and operable with either the circuit of FIG. 8 or the circuit of FIG. 9.
Figure 14A:
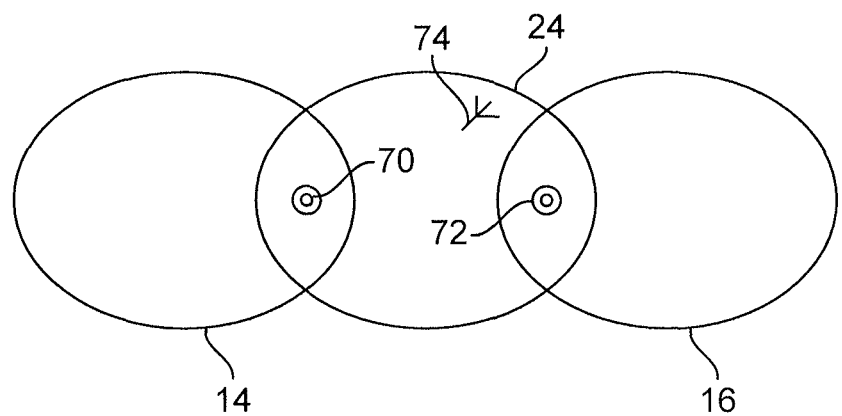
Figure 14B:
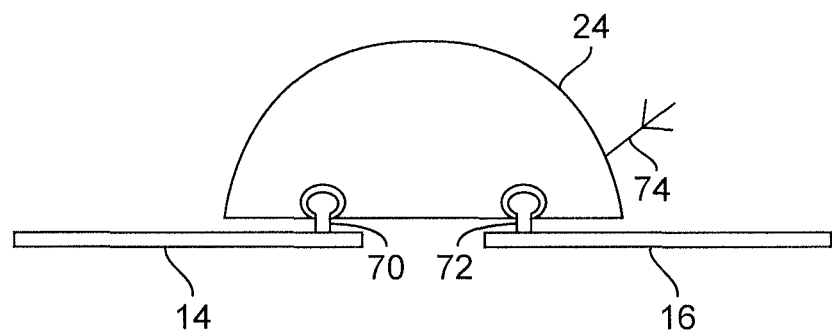

Turning now to FIGS. 14A and 14B there can be seen a pair of active and passive electrodes 14, 16 which are provided with terminals 70, 72 onto which a respective stimulation signal generator 24 is clipped so that it has electrical contact to the two terminals 70, 72. The stimulation signal generator 24 can, for example, be designed as shown in FIG. 10 and can have its own antenna 74 which can be simply a receiver antenna 27 as shown in FIG. 10, or an antenna for a combined receiver/transmitter 27, 28 which is also indicated in FIG. 10.

Figure 15:
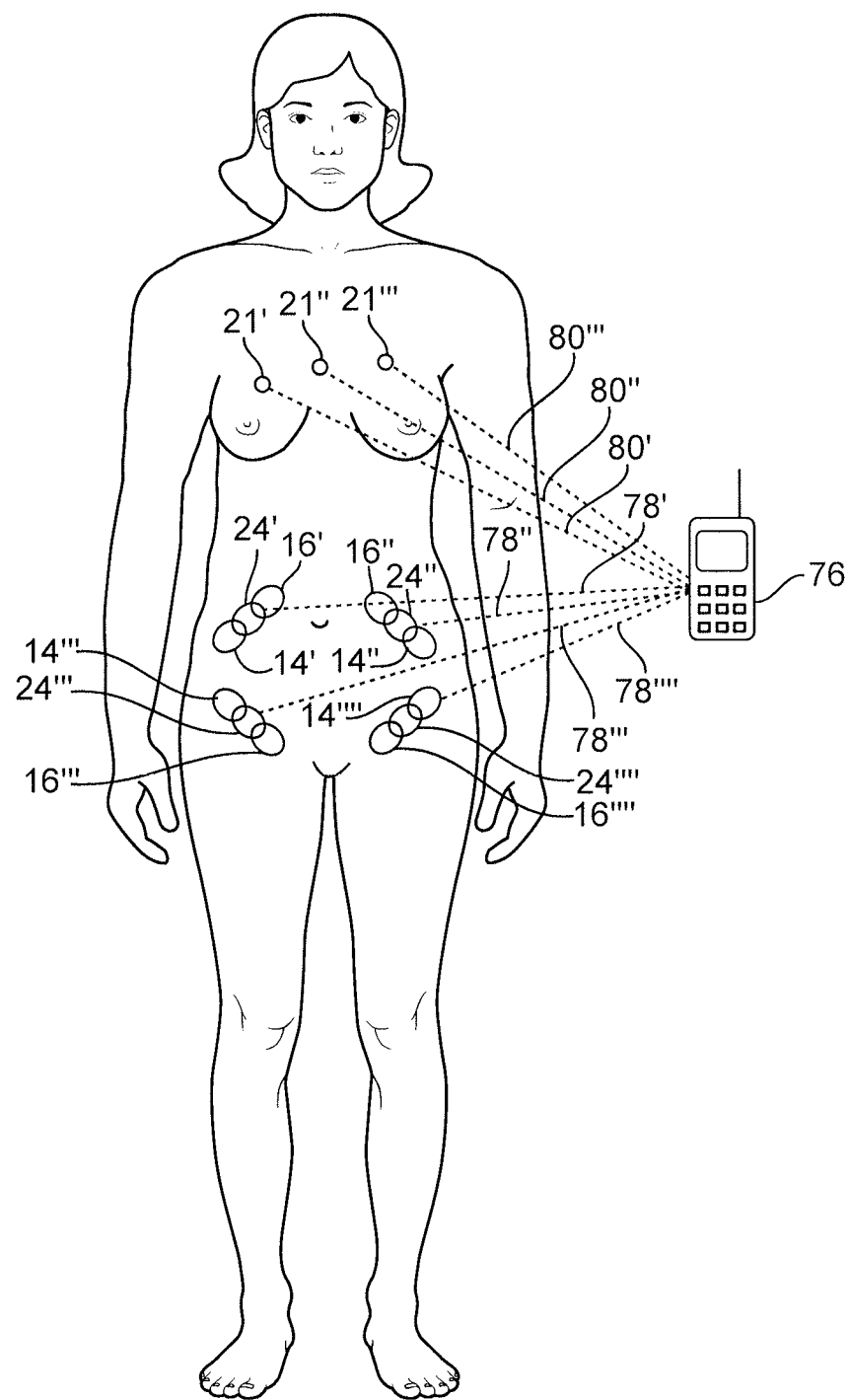
FIG. 15 is a diagram showing a patient provided with four pairs of active and passive electrodes.
Figure 16A:
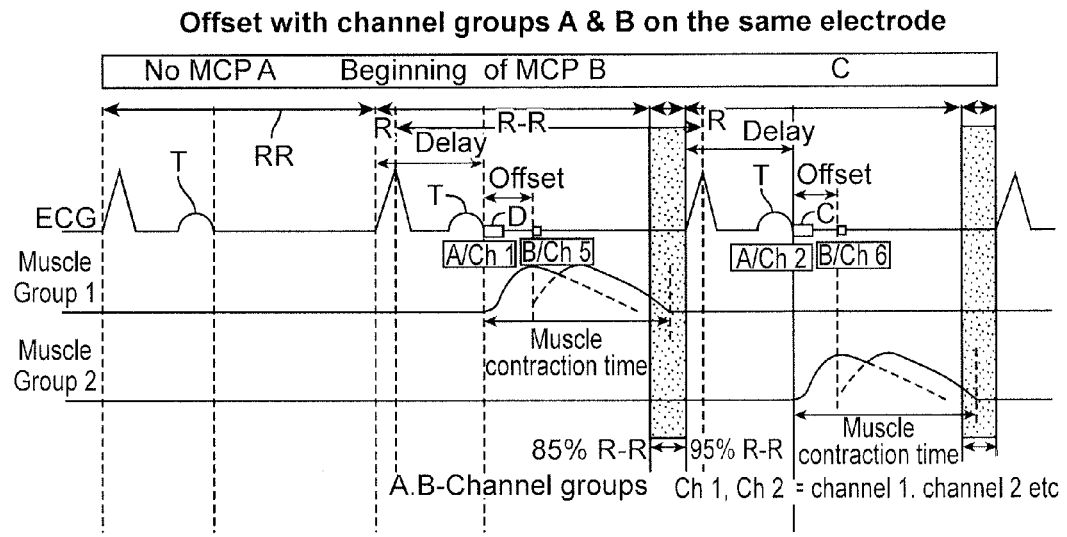
FIGS. 16A and 16B are diagrams similar to FIG. 11A but showing how the stimulation signals are applied to each pair of active electrodes in turn, the diagram of FIGS. 16A and 16B corresponding to FIGS. 6 and 8 of the international application published as WO 2005/044373.

Turning now to FIG. 15 there can be seen four pairs of active and passive electrodes 14', 16'; 14", 16"; 14''', 16'''; 14'''', 16'''', each provided with a respective stimulation signal generator 24', 24"; 24''', 24''''. Instead of providing each stimulation signal generator 24 with its own antenna 74, which can be a receiver antenna or a transceiver antenna, each of the stimulation signal generators could be connected to a transceiver 76 illustrated here in the form of a mobile phone, and indeed via leads 78', 78", 78''', 78''''. Equally, if a mobile phone is used in this way it can be connected to the ECG electrodes 21', 21", 21''' or to any other suitable sensing system. Again, the connection in this case is by way of leads 80', 80", 80'''. Because the leads 78', 78", 78''', 78'''' and 80', 80" and 80''' are optional they are shown in broken lines. Since very light leads can be used they do not pose a significant inconvenience for the patient FIGS. 16A and 16B now illustrate how the pairs of active and passive electrodes are energized. It is noted that FIG. 16B refers to channels 1, 2, 3 and 4 which are the channels which are associated with the four electrode pairs 14', 16'; 14", 16"; 14''', 16'''; 14'''', 16'''' and the associated stimulation signal generators 24', 24"; 24''' in FIG. 15.

The channels 5, 6, 7 and 8, which are an optional extra, could be associated with four further pairs of active/passive electrodes with associated stimulation signal generators (not shown). As described in WO 2005/044373, such systems can be used to improve blood transport to different areas of the body or to improve lymph transport from various areas of the body. In order to achieve such transport it is necessary for the electrical stimulation signals in the group of channels 5 to 8 to be offset from those in the channels 1 to 4. This will not be explained further here because the concept is described and claimed in detail in the above referenced PCT application.

Figure 16B:
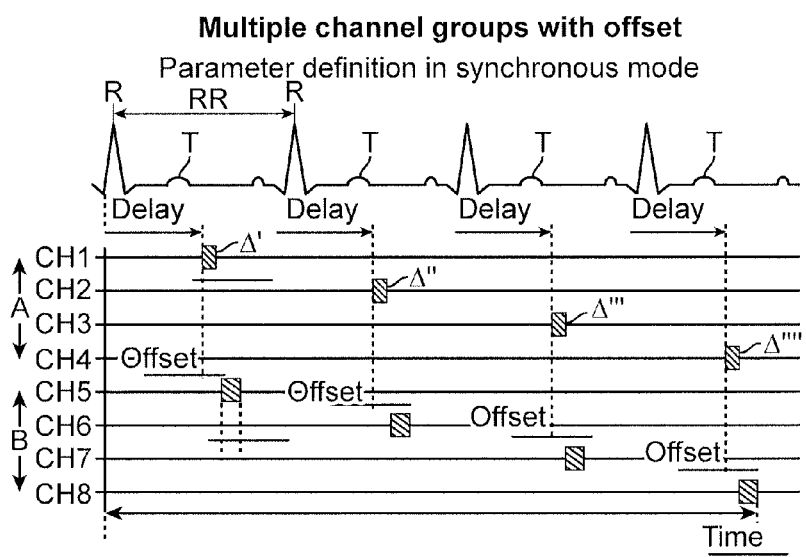
Figure 17A:
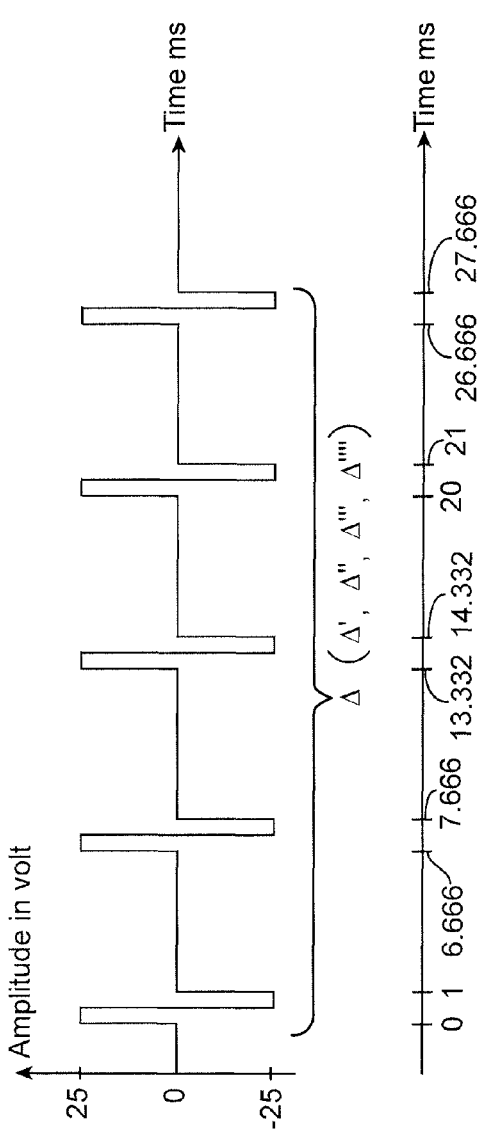
FIGS. 17A and 17B are diagrams corresponding to FIGS. 5A and 5B of WO 2005/044374 showing one possible scheme of electrical stimulation provided to one pair of active and passive electrodes for one heartbeat of a patient.

The schematic representation of an ECG trace at the top of FIG. 16B shows four R-R peaks corresponding to four heartbeats and it can be seen that a first electrical stimulation signal D' (corresponding to D in FIG. 11A) is applied to the first electrode pair 14', 16' via channel 1 during a first heartbeat. A second train of electrical stimulation pulses D" is then applied during a second subsequent heartbeat via the channel 2 to the pair of electrodes 14", 16". During the third heartbeat a further train of electrical stimulation pulses D''' is applied via channel 3 to the third pair of electrodes 14''', 16''' and during a fourth heartbeat a further train of electrical stimulation pulses D'''' is applied via the channel 4 to the fourth pair of electrodes 14'''', 16''''. During a fifth heartbeat (not shown) a further train of electrical stimulation pulses corresponding to D' is again applied via channel 1 to the first pair of electrodes 14', 16' and so on.

FIG. 16A again illustrates the offset between the two channel groups channels 1 to 4 and channels 5 to 8, and it can be seen that the stimulation signal applied to muscle group 1, for example the muscle group with which the electrode pair 14', 16' cooperates, has a duration which is considerably shorter than the muscle contraction which it generates.

In FIG. 11A and in FIGS. 16A and 16B there is shown a relatively straightforward method of muscle stimulation involving five individual biphasic pulses D. These five individual biphasic pulses are illustrated again in FIG. 17A, together with possible values for the amplitude of the biphasic pulses in volts and durations shown in milliseconds.

It is, however, possible to use additional stimulating pulses after the initial group of stimulating pulses D in order to prolong the muscle contraction but minimizing the electrical input into the patient which is beneficial both for the patient and for the lifetime of the batteries involved in the stimulation signal generators.

Figure 17B:
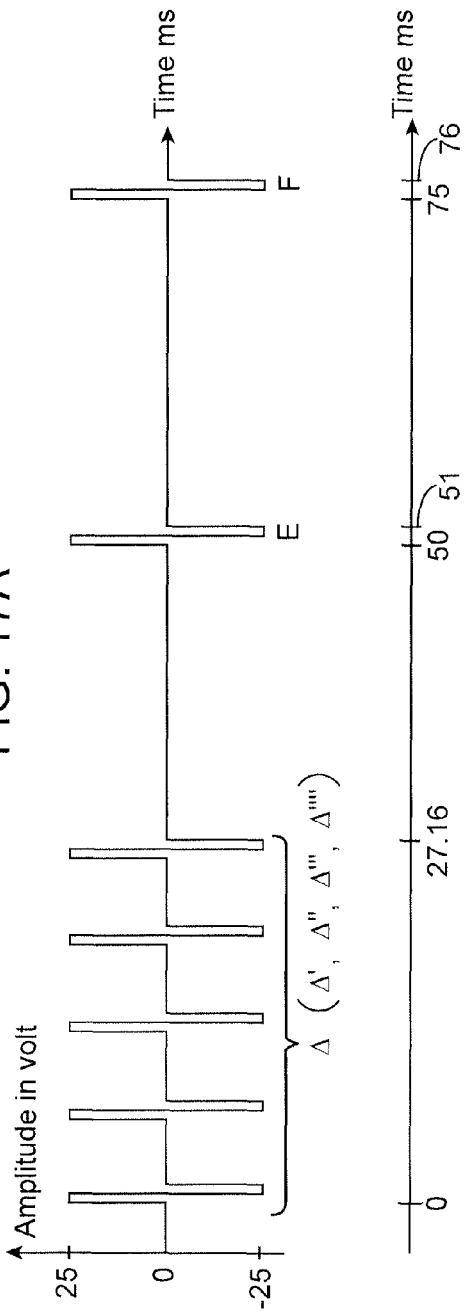

In the scheme shown in FIG. 17B the first group of pulses D is followed by individual pulses E, F which, in this example, are single biphasic pulses identical to the individual biphasic pulses of the group D, but with a greater pulse interval between the pulses. In practice there can be many more individual pulses such as E and F. Also there are a large number of different variants of such stimulation schemes and these are explained in detail in WO 2005/044374. They will not be discussed here in detail.

What is claimed is:

1. An apparatus configured for cardio-synchronised stimulation of skeletal or smooth muscle, but excluding heart muscles, in a counterpulsation mode of a patient having a cardiovascular system and a heart having a heart rate, the apparatus comprising:
   at least one active electrode and at least one passive electrode configured for attachment to said patient at positions at which the electrodes are in communication with said skeletal or smooth muscle when said skeletal or smooth muscle is in its original, natural position within the patient;
   a signal processor configured to produce control signal information relating to stimulation signals to be applied to said at least one active electrode in the counterpulsation mode;
   a sensing system configured to sense information relating to performance of the patient's heart, the information comprising at least the heart rate, and to transmit information signals to said signal processor;
   at least one stimulation signal generator associated with said active electrode and configured to generate the stimulation signals, the stimulation signals being provided at the active electrode in synchronization with the heart rate in the counterpulsation mode to thereby stimulate the skeletal or smooth muscle when the skeletal or smooth muscle is in the original, natural position within the patient; and
   a wireless transmitter configured to transmit said control signal information from said signal processor to said at least one stimulation signal generator, whereby said stimulation signal generator applies the stimulation signals to said active electrode in the counterpulsation mode in accordance with said control signal information.

2. The apparatus in accordance with claim 1, wherein said information relating to the performance of the heart is selected from the group consisting of heart rate information, electrocardiogram (ECG) information, ECG derived information, ECG information and information resulting from electrical stimulation, ECG derived trigger signals, R-R information, end of T-wave information, blood pressure information, and blood pressure derived information.

3. The apparatus in accordance with claim 1, wherein said sensing system comprises at least one of an invasive sensor, an intercavity sensor, a non-invasive sensor, a body surface sensor, and a remote sensing system detached from the patient's body.

4. The apparatus in accordance with claim 3, further comprising a remote sensing system, wherein said signal processor is integrated into said remote sensing system.

5. The apparatus in accordance with claim 1, further comprising a medical evaluation unit.

6. The apparatus in accordance with claim 5, said signal processor being adapted to transmit said information to the medical evaluation unit by one of wireless transmission and a wired connection.

7. The apparatus in accordance with claim 5, said medical evaluation unit being adapted to transmit signal configuration information to said signal processor by one of wireless transmission and a wired connection and said signal processor being adapted to take account of said signal configuration information when generating said control signal information.

8. The apparatus in accordance with claim 1, wherein the at least one of active electrode comprises a plurality of active electrodes and said at least one stimulation signal generator comprises a respective stimulation signal generator for each active electrode, said signal processor being configured to transmit a respective control signal uniquely associated with a respective one of said active electrodes to each said stimulation signal generator.

9. The apparatus in accordance with claim 1, wherein said signal processor is configured to transmit control signal information for a train of stimulation signals applied to one of the active electrodes, said control signal information being selected from the group consisting of:
   amplitude of the stimulation signals,
   frequency of the stimulation signals,
   duration of the train of the stimulation signals,
   width of the individual stimulation signals of the train
   delay of the train of the stimulation signals relative to a reference selected for counterpulsation stimulation, and
   a recognition code by which said stimulation signal generator recognizes that said control signal information is intended for it.

10. The apparatus in accordance with claim 9, further comprising a means provided at said signal processor for receiving and storing at least one of a program for processing said control signal information, any subsequent changes to said program, and a new program for processing said control signal information.

11. The apparatus in accordance with claim 1, wherein the or each said stimulation signal generator includes at least some of the following items:
   its own controller,
   its own clock,
   its own receiver antenna (RX),
   a power circuit,
   a battery,
   a transmitter (RX),
   means for data storage,
   means for program storage and
   a signal generator trigger.

12. The apparatus in accordance with claim 1, wherein a display is provided at at least one of said signal processor, said configuration input associated with the signal processor, said stimulation signal generator and a medical evaluation unit associated with said apparatus, said display being for the display of at least said control signal information.

13. The apparatus in accordance with claim 12, wherein said display is adapted to display data representing an image of the electrical stimulation applied to said patient.

14. The apparatus in accordance with claim 13, wherein said display is adapted to display one of an actual ECG-trace and a representation of an ECG-trace with said image superimposed thereon.

15. The apparatus in accordance with claim 5, wherein said medical evaluation unit has an associated printer for printing said data.

16. The apparatus in accordance with claim 1, wherein a code is uniquely associated with said sensing system, said signal processor, and said electrical stimulation signal generator.

17. The apparatus in accordance with claim 1, wherein said stimulation signal generator comprises a member of the group consisting of a mobile phone, a personal digital assistant with phone function, and any dedicated or standard piece of equipment comprising a transceiver, a microprocessor, a memory for storing software and data, a battery or other source of power, a clock, and necessary interface(s) for connection to the active and passive electrodes.

18. The apparatus in accordance with claim 1, wherein said signal processor comprises a member of the group consisting of a mobile phone, a personal digital assistant with phone function, and any dedicated or standard piece of equipment comprising a transceiver, a microprocessor, a memory for storing software and data, a battery or other source of power, and a clock.

19. The apparatus in accordance with claim 5, wherein said medical evaluation unit comprises a member of the group consisting of is one of a personal computer, a mainframe computer, a series of interlinked computers, any of the foregoing with an inbuilt transceiver, a personal digital assistant with phone function, and any dedicated or standard piece of equipment comprising a transceiver, a microprocessor, a memory for storing software and data, a battery or other source of power, and a clock.

* * * * *